United States Patent
Zhou et al.

(10) Patent No.: US 10,975,403 B2
(45) Date of Patent: Apr. 13, 2021

(54) BIOSYNTHESIS OF ERIODICTYOL FROM ENGINEERED MICROBES

(71) Applicant: Conagen Inc., Bedford, MA (US)

(72) Inventors: Rui Zhou, Acton, MA (US); Xiaodan Yu, Lexington, MA (US); Steven Chen, Rancho San Margarita, CA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 16/032,800

(22) Filed: Jul. 11, 2018

(65) Prior Publication Data

US 2019/0048374 A1 Feb. 14, 2019

Related U.S. Application Data

(60) Provisional application No. 62/542,843, filed on Aug. 9, 2017.

(51) Int. Cl.

| | |
|---|---|
| *C12N 15/70* | (2006.01) |
| *C12N 15/54* | (2006.01) |
| *C12N 9/06* | (2006.01) |
| *C12N 9/24* | (2006.01) |
| *C12P 17/06* | (2006.01) |
| *A61K 8/99* | (2017.01) |
| *A61K 8/49* | (2006.01) |
| *A23L 27/00* | (2016.01) |
| *A23L 27/30* | (2016.01) |
| *A23L 33/10* | (2016.01) |
| *A61Q 19/00* | (2006.01) |
| *C07D 311/32* | (2006.01) |
| *C12N 15/81* | (2006.01) |
| *A61Q 5/00* | (2006.01) |

(52) U.S. Cl.
CPC .............. *C12P 17/06* (2013.01); *A23L 27/36* (2016.08); *A23L 27/86* (2016.08); *A23L 33/10* (2016.08); *A61K 8/498* (2013.01); *A61K 8/99* (2013.01); *A61Q 19/00* (2013.01); *C07D 311/32* (2013.01); *C12N 9/0028* (2013.01); *C12N 15/70* (2013.01); *C12N 15/81* (2013.01); *A61K 2800/10* (2013.01); *A61Q 5/00* (2013.01); *C12Y 105/0103* (2013.01)

(58) Field of Classification Search
CPC ...... C12N 9/0028; C12N 15/81; C12N 15/70; A61K 2800/10; A61K 8/99; C07D 311/32; C12P 17/06; C12Y 105/0103
USPC ........... 435/189, 124, 125, 147, 196, 252.2, 435/252.31, 252.33, 320.1; 536/23.2
See application file for complete search history.

(56) References Cited

U.S. PATENT DOCUMENTS

| | | |
|---|---|---|
| 5,578,476 A | 11/1996 | Zenno et al. |
| 5,959,178 A | 9/1999 | Fritig et al. |
| 6,274,372 B1 | 8/2001 | Gray et al. |
| 2007/0243140 A1 | 10/2007 | Giamalva et al. |
| 2008/0274959 A1 | 11/2008 | Haltli et al. |
| 2008/0305052 A1 | 12/2008 | Ley et al. |
| 2008/0317923 A1 | 12/2008 | Ley et al. |
| 2010/0047887 A1 | 2/2010 | Achkar et al. |
| 2011/0097447 A1 | 4/2011 | Roy et al. |
| 2011/0166335 A1 | 7/2011 | Corbin et al. |
| 2014/0057325 A1 | 2/2014 | Nielsen et al. |
| 2014/0141044 A1 | 5/2014 | Bhatt et al. |
| 2014/0342043 A1 | 11/2014 | Bell et al. |
| 2015/0111298 A1 | 4/2015 | Lattemann et al. |
| 2015/0184205 A1 | 7/2015 | Yan et al. |
| 2015/0322465 A1 | 11/2015 | Ramaen et al. |
| 2016/0044805 A1 | 2/2016 | Fan |
| 2016/0097063 A1 | 4/2016 | Li et al. |
| 2018/0135029 A1 | 5/2018 | Wessjohann et al. |

FOREIGN PATENT DOCUMENTS

| | | |
|---|---|---|
| KR | 20090131845 A | 12/2009 |
| WO | 2016044805 A1 | 3/2016 |
| WO | 2017055573 A1 | 4/2017 |

OTHER PUBLICATIONS

Kisselev L., Structure, 2002, vol. 10: 8-9.*
Kwiatkowski et al., Biochemistry 38:11643-11650, 1999.*
Wristlock et al., Quarterly Reviews of Biophysics 2003, vol. 36 (3): 307-340.*
Davos et al., Proteins: Structure, Function and Genetics, 2000, vol. 41: 98-107.*
International Search Report dated Feb. 7, 2019; International Application No. PCT/US18/41745; International Filing Date: Jul. 12, 2018.
Amor IL et al., (2010) Biotransformation of naringenin to eriodictyol by *Saccharomyces cerevisiae* functionally expressing flavonoid 3' hydroxylase. Nat Prod Commun. 5:1893-8, Abstract.
Galan B., et al., . (2000) Functional analysis of the small component of the 4-hyroxylacetate 3-monooxygenase of *Escherichia coli* @: a prototype of a new Flavin: NAD(P)H reductase subfamily. Journal of Bacteriology 182: 627-636.
Berner M, et al., (2006) Genes and Enzymes Involved in Caffeic Acid Biosynthesis in the Actinomycete Saccharothrix espanaensis. Journal of Bacteriology 188: 2666-2673.
Bravo L (1998) Polyphenols: chemistry, dietary sources, metabolism, and nutritional significance. NUTR REV 56:317-333.
Brugliera F., et al., (1999) Isolation and characterization of a flavonoid 3'-hydroxylase cDNA clone corresponding to the Ht1 locus of Petunia hybrid. Plant J 19: 441-451.

(Continued)

*Primary Examiner* — Robert B Mondesi
*Assistant Examiner* — Mohammad Y Meah
(74) *Attorney, Agent, or Firm* — Wolf, Greenfield & Sacks, P.C.; W. John Keyes

(57) ABSTRACT

The present invention relates to the production of eriodictyol via bioconversion.

29 Claims, 19 Drawing Sheets

Specification includes a Sequence Listing.

(56) References Cited

OTHER PUBLICATIONS

Cao H, Chen X, Jassbi AR and Xiao J (2015) Microbial biotransformation of bioactive flavonoids. Biotechnology Advances 33: 214-223.
Chu LL, et al., (2016) Hydroxylation of diverse flavonoids by CYP450 BM3 variants: biosynthesis of eriodictyol from naringenin in whole cells and its biological activities. Microb Cell Fact. 15:135.
Du J et al., (2011), Engineering microbial factories for synthesis of value-added products, J Ind Microbiol Biotechnol. 38: 873-90.
Lee ER, Kim JH, Kang YJ, and Cho SG (2007) The anti-apoptotic and anti-oxidant Effect of eriodictyol on UV-Induced apoptosis in keratinocytes. Biol Pharm Bull 30: 32-37.
Lee H, Kim BG and Ahn JH (2014) Production of bioactive hydroxyflavones by using monooxygenase from Saccharothrix espanaensis. Journal of Biotechnology 176: 11-17.
Ley JP, Krammer G, Reinders G, Gatfield IL, and HJ Bertram (2005) Evaluation of bitter masking flavanones from Herba Santa (Eriodictyon californicum (H. & A.) Torr., Hydrophyllaceae). J Agri Food Chem 53:6061-66.
Kaltenbach M, Schröder G, Schmelzer E, Lutz V, Schröder J. (1999), Flavonoid hydroxylase from Catharanthus roseus: cDNA, heterologous expression, enzyme properties and cell-type specific expression in plants. Plant J. 19:183-93.
Kasai N., et al., (2009) Enzymatic properties of cytochrome P450 catalyzing 3'-hydroxylation of naringenin from the white-rot fungus Phanerochaete chrysosporium, Biochem Biophys Res Commun. 387:103-08.
Kim BG., et al., (2005). Multiple regiospecific methylations of a flavonoid by plant O-methyltransferases expressed in *E. coli*. Biotechnol. Lett. 27: 1861-64.
Lamartiniere CA (2000) Protection against breast cancer with genistein: a component of soy. Am J Clin Nutr 71:1705S-1707S.
Le Marchand L (2002) Cancer preventive effects of flavonoids—a review. Biomed Pharmacother 56:296-301.
Ley J.P. et al., New Bitter-Masking Compounds: Hydroxylated Benzoic Acid Amides of Aromatic Amines as Structural Analogues of Homoeriodictyol, J. Agric. Food Chem., (2006) 54 (22): 8574-79.
Lim E-K., et al., (2004) *Arabidopsis* glycosyltransferases as biocatalysts in fermentation for regioselective synthesis of diverse quercetin glucosides. Biotechnol. Bioeng. 87: 623-31.
Lin Y, Jain R and Yan Y (2014) Microbial production of antioxidant food ingredients via metabolic engineering. Current Opinion in Biotechnology 26: 71-78.
Lin Y and Yan Y (2014) Biotechnological Production of Plant-Specific Hydroxylated Phenylpropanoids. Biotechnology and Bioengineering 111:1895-1899.
Matsuo M, Sasaki N, Saga K, Kaneko T (2005) Cytotoxicity of flavonoids toward cultured normal human cells. Biol Pharm Bull. 28 253-259.
Ogata S, Miyake Y, Yamamoto K, Okumura K, Taguchi H (2000) Apoptosis induced by the flavonoid from lemon fruit (*Citrus limon BURM. f.*) and its metabolites in HL-60 cells. Biosci Biotechnol Biochem 64: 1075-1078.
Steven G. Van Lanen, Shuangjun Lin, Geoff P. Horsman and Ben Shen (2009) Characterization of SgcE6, the Flavin reductase component supporting FAD-dependent halogenation and hydroxylation in the biosynthesis of the enediyne antitumor antibiotic C-1027. FEMS Microbiology Letter 300: 237-241.
Winkel-Shirley B (2001) Flavonoid biosynthesis. A colorful model for genetics, biochemistry, cell biology, and biotechnology. Plant Physiol. 126: 485-493.
Crespo I. et al., Differential effects of dietary flavonoids on reactive oxygen and nitrogen species generation and changes in antioxidant enzyme expression induced by proinflammatory cytokines in Chang Liver cells. Food Chem. Toxicol. (May 2008);46(5):1555-69.
[No Author Listed], Pyoverdin chromophore biosynthetic protein pvcC [*Streptomyces* sp. 2112.3). NCBI Reference Sequence: WP_093492121.1, Jul. 29, 2017. [retrieved on Feb. 7, 2020]. 1 page.
[No Author Listed], caffeic acid/5-hydroxyferulic acid O-methyltransferase [Populus tremuloides]. Genbank Acession No. AAB61731.1, Jun. 29, 1996. [retrieved on Apr. 15, 2020]. 2 pages.
Berner et al., Genes and enzymes involved in caffeic acid biosynthesis in the actinomycete Saccharothrix espanaensis. J Bacteriol. Apr. 2006;188(7):2666-73.
Lin et al., Cloning and functional analysis of caffeic acid 3-O-methyltransferase from rice (*Oryza sativa*). J. Pestic. Sci., 2006;31(1):47-53.
Strobel et al., Complete genome sequence of Saccharothrix espanaensis DSM 44229(T) and comparison to the other completely sequenced Pseudonocardiaceae. BMC Genomics. Sep. 9, 2012;13:465. doi: 10.1186/1471-2164-13-465.

* cited by examiner

FIG.4

```
                                    1         2         3         4         5         6         7         8
                                    |         |         |         |         |         |         |         |
M-------QLDEQRL-----REIDAMASLSAAVNIITT-EGDAGQGITATAVCSVTDTPPSLMVCINAN          HpaC
M--------NAATETKVHDLLDAEGRDVRDARELRNVLGQFATGVTVITTRTADGRNVGVTANSFSSLSLSPALVLMWSLART   PpFR
MMTVYDSALTMEET----------TIDAMSRFATGVSVVTV-GGEMTH--GMTANAFTCVSLDPPLVLCCVARK           SeFR 90        100       110       120       130       140       150       160
            |         |         |         |         |         |         |         |
SAMNPVFQGNGKLCVNVLNHEQELMARHFAGMTG------MAMEERFSL--------SCWQKGPLAQPVLKGSLASLE-GEIR  HpaC
APSLKVFCSASHFAINVLGAHQLHLSEQFARAAADKFAGVAHSYGK---------A------GAPVLDDVVAVLVCRNVT    PpFR
ATMHAAIEGARRFAVSVMGGDQERTARYFADKRR--PRGRAQFDVVDWQPGPHT--------GAPLLSGALAWLE-CEVA    SeFR 170       180       190       200       210
            |         |         |         |         |
D-VQAIGTHLVYLVEIKNIILSAEGHGLLIYFKRRFHPVMLEMEAAI------.                HpaC
Q-YEG-GDHLIFIGEIEQYRYSG-AEPLVFHAGQYRGLGSNRAESVLKHE---.                PpFR
QWHEG-GDHTIFLGRVLGCRRGPDSPAILFYGSDFHQIR--------------                 SeFR
```

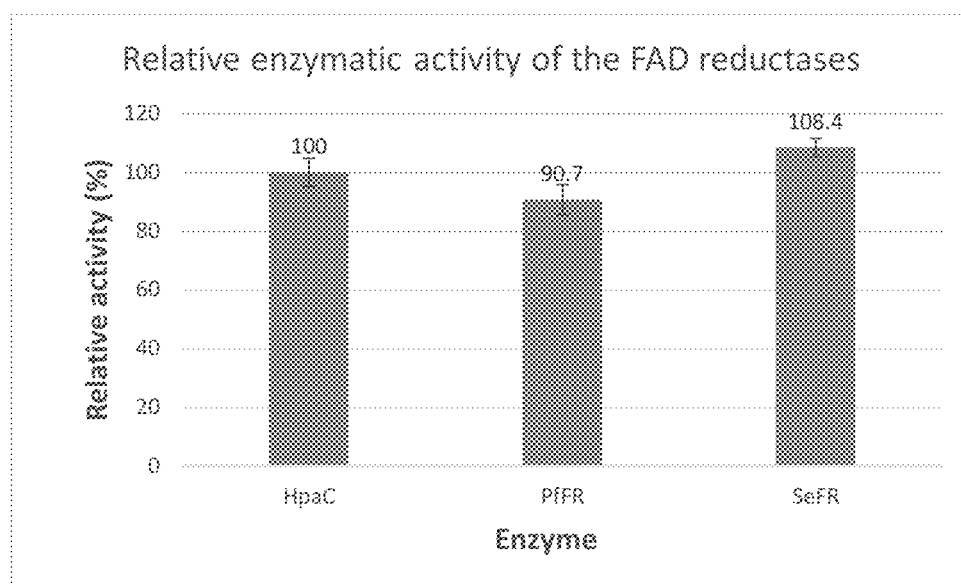
Fig. 6. Relative enzymatic activity of the FAD reductases compared to HpaC

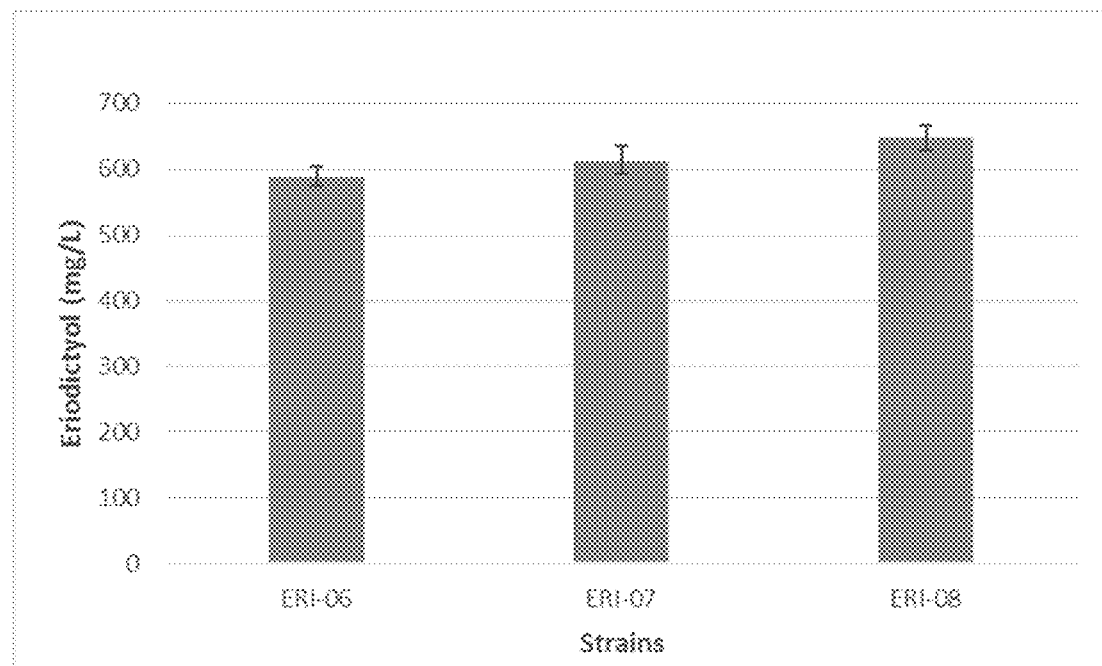
Fig. 11
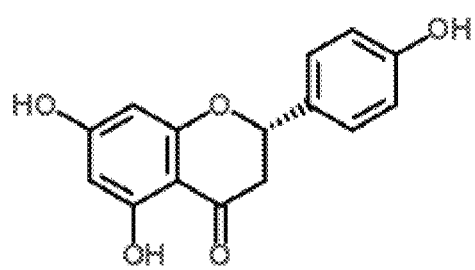
Fig. 12. Naringenin

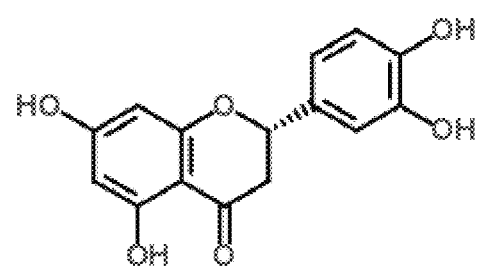
Fig. 13 Eriodictyol

BIOSYNTHESIS OF ERIODICTYOL FROM ENGINEERED MICROBES

CROSS-REFERENCE TO RELATED APPLICATIONS

This application claims priority to U.S. Provisional Patent Application No. 62/542,843, filed Aug. 9, 2017, entitled BIOSYNTHESIS OF ERIODICTYOL FROM ENGINEERED MICROBES, the disclosures of which are hereby incorporated by reference in their entirety.

FIELD OF THE INVENTION

The field of the invention relates to methods and processes useful in the production of eriodictyol from precursor molecules, specifically from naringenin. More specifically, the production of eriodictyol from naringenin via in vivo enzymatic conversion.

BACKGROUND OF THE INVENTION

The present invention is focused on the conversion of naringenin to eriodictyol. The present disclosure relates to the synthesis of eriodictyol via microbial fermentation.

Flavonoids are one of the most numerous and structurally diverse natural products present in the plant kingdom. They are known to have a variety of multi-beneficial medicinal and chemo-preventive effects on human health. Flavonoids have been shown to act as antioxidants, antibacterials, anti-inflammatory agents, and have demonstrated anticancer properties. However, the pharmaceutical application of these compounds is limited, because of their low water solubility and overall instability. Chemically, flavones are 2-phenyl-4H-1-benzopyran-4-ones in which hydroxyl groups may be present or even missing at various positions of the rings. One example of a flavone is apigenin of which the chemical name is 2-(p-hydroxyphenyl)-4H-1-(5,7-dihydroxybenzopyran-4-one. Accordingly, this definition includes flavans, flavan-3-ols (catechols), flavan-3,4-diols (leucoanthocyanidines), flavones, flavonols and flavonones in the traditional sense. The flavones of interest in the current invention are: naringin, naringenin and eriodictyol.

Flavonoids are secondary plant metabolites synthesized using the phenylpropanoid pathway (Winkel-Shirley, 2001) and are present in a great variety of plants. Flavonoid-derived compounds have drawn much attention because of their use as health-promoting components in the human diet. This is due to the variety of their cancer chemo preventive, antioxidant and anti-asthmatic activities (Bravo 1998; Lamartiniere 2000; File et al. 2001; and, Le Marchand 2002). However, the exact profile and amounts of specific flavonoids in plants differs greatly among species.

As stated above, flavonoids are important natural compounds with diverse biologic activities. Flavonoids derived from citrus sources constitute a potentially medically important series of flavonoids. Naringenin belongs to this series of flavonoids and has been found to display strong anti-inflammatory and antioxidant activities in mammalian systems. Several lines of investigation suggest that another citrus-derived flavonoid, naringin, and naringin supplementation is beneficial for the treatment of obesity, diabetes, hypertension, and metabolic syndrome in humans. Several molecular mechanisms underlying these beneficial activities have been elucidated. However, the mechanism of their effect on obesity and metabolic disorder remains to be fully determined.

Naringin

Naringin is a flavanone-7-O-glycoside that can be enzymatically modified to become naringenin. Naringenin occurs naturally in citrus fruits, especially in grapefruit, where naringin is responsible for the fruit's bitter taste. In commercial grapefruit juice production, the enzyme naringinase can be used to remove the bitterness created by naringin.

Naringin inhibits some drug-metabolizing cytochrome P450 enzymes, including CYP3A4 and CYP1A2, which may result in systemic drug-drug interactions. Ingestion of naringin and related flavonoids can also affect the intestinal absorption of certain drugs, leading to either an increase or decrease in circulating drug levels. To avoid interference with drug absorption and metabolism, the consumption of citrus (especially grapefruit) and other juices with medications is contraindicated in patients with medications that can be affected by citrus flavonoids.

Naringenin

Naringenin is a flavanone and can be found in grapefruit, oranges and the skin of tomatoes. This bioflavonoid is difficult to absorb on oral ingestion. However, when ingested, it has been shown to have an inhibitory effect on the human cytochrome P450 isoform CYP1A2. This beneficial property may also extend to being a potent inhibitor of the benzo(a)pyrene metabolizing enzyme benzo(a)pyrene hydroxylase (AHH). Similarly, naringenin has also been shown to reduce oxidative damage to DNA in vitro and in animal studies. Naringenin has also been shown to reduce hepatitis C virus production by infected hepatocytes (liver cells) in cell culture. This seems to be secondary to naringenin's ability to inhibit the secretion of very-low-density lipoprotein by the cells. Naringenin also protects LDLR-deficient mice from the obesity effects of a high-fat diet. Naringenin lowers the plasma and hepatic cholesterol concentrations by suppressing HMG-CoA reductase and ACAT in rats fed a high-cholesterol diet.

Eriodictyol

Eriodictyol is also a flavonoid compound found in some plants. Compared to naringenin it has an additional hydroxylation. It also has higher bioactivity. Eriodictyol is capable of masking bitter flavors and is widely used in medicine and food production.

In the extraction industry eriodictyol is taken from the Yerba Santa (*Eriodictyon californicum*) plant (Ley et al 2005). When used in tests eriodictyol was demonstrated to significantly decrease the bitter taste of caffeine without exhibiting intrinsic strong flavors or taste characteristics, which had a great potential in the modification of the taste profiles of food, drink and medicine. Moreover, eriodictyol has been shown to possess higher biological activity and have more anti-cancer activity than many other flavonoids (Lee et al 2007; Chu et al. 2016). Regarding the anti-cancer effect, eriodictyol was considered to have little or no effect on normal cultured human cells (Matsuo et al. 2005), but was shown to induce apoptotic DNA ladder formation, chromatin condensation and cytotoxicity in HL-60 leukemic cells (Ogata 2000).

As a secondary metabolite, flavonoids are often produced in small or variable amounts in particular plant species, which hampers their cost-effective isolation, and broad application. Moreover, some of these species are endangered in their natural habitats, thus further limiting the availability of some plant metabolites for commercial use.

In terms of additional utility in the pharmaceutical space it has been found that eriodictyol is an a TRPV1 antagonist and could be used as an analgesic. The vanilloid 1 receptor (TRPV1) is a calcium-permeable channel responsible for the transduction and modulation of acute and chronic pain signaling. As such, this receptor is a potential target for the treatment of several pain disorders.

It is known that in plants eriodictyol can be derived by the hydroxylation of naringenin in plants by the catalysis of flavonoid 3'-hydroxylase (F3'H), a cytochrome P450-dependent monooxygenase (Brugliera et al., 1999; Kaltenbach et al. 1999). In past decades, biocatalytic hydroxylation of naringenin was achieved due to the identification and engineering of some cytochrome P450 hydroxylases from plants and microorganisms (Kasai et al., 2009; Amor et al. 2010; Chu et al. 2016). However, as P450 hydroxylase is a membrane-bound protein, its activity depends on P450-reductase and heme biosynthesis, functional expression of P450s in prokaryotic system is challenging (Oeda et al., 1985). Recently some efforts have been taken to identify non-P450 hydroxylase for the bioconversion of naringenin to eriodictyol. Lin and Yan (2014) found HpaBC, which was initially identified as a two-component monooxygenase that catalyzes the ortho-hydroxylation of 4-hydroxyphenylacetate in *Escherichia coli*, could hydroxylate naringenin to eriodictyol (Lin and Yan 2014). Lee et al (2014) showed SAM5, a monooxygenase from *Saccharothrix espanaensis* catalyzing the hydroxylation of caffeic acid to ferulic acid, had the activity toward naringenin. However, the reported titers of eriodictyol via these non-P450 hydroxylase are low for scale-up production use. The expressed SAM5 enzyme alone showed low activity to flavonoid in *E. coli* cells. Co-expression of a P450 reductase was a way to increase the activity. However, the stimulation of hydroxylation of flavonoids through this way is limited and only approximately 34 to 50% enhancement was observed (Lee et al 2014).

Collectively, the purpose of this disclosure is to demonstrate the production of naringenin and eriodictyol via bioconversion and provide techniques that will enable an increased volume of such compounds to be available for industrial use as well as research in the pharmaceutical and cosmeceutical arena.

In this way, the limited quality and supply of eriodictyol can be better addressed by bio-conversion, where natural enzymes, or specific microbes can be modified to carry needed enzymes and use commercially significant fermentation processes to specifically increase the production of flavonoids of interest.

According to the current invention, a practical approach to improve the production of eriodictyol that will allow its economical production via bioconversion. Moreover, it is difficult to obtain sufficient quantities of specific flavonoids for use as a medicinal food or as a precursor for the development of new medicines since composition and quantity vary greatly due to weather conditions and according to geography even in plants known to produce them. To address this problem and supply sufficient amounts of bio-active flavonoids, one practical and promising approach is bio-transformation through bioconversion (Lim et al, 2004; Kim et al 2005). This will reverse the limited availability and high cost of sourcing these compounds from the plant world. This relative increased abundance will allow the production of several flavonoids for use in the food, pharmaceutical and cosmetics industries.

Accordingly, there is a need for the flavonoids provided herein to be developed as commercial products and for such compounds to utilize a relative common starting substrate, such as naringin as a starting molecule, so that such production of desirable flavonoids can be commercially as cost effective as possible. The present disclosure provides a method of producing eriodictyol from naringin and/or naringenin.

Going further, the extraction process from plants, typically employs solid-liquid extraction techniques using solvents like hexane, chloroform, and ethanol for recovery. However, solvent extraction is itself energy intensive, leads to problems of toxic waste disposal, requires extensive acreage for the plants themselves to be grown and yields a product that requires further purification for minor constituents to be recovered. Thus, new production methods are also needed to reduce costs of eriodictyol production and lessen the environmental impact of large scale cultivation and processing. One such potential solution is the use of fermentation bio-conversion technology that allows the production in certain microbial species that increases the selectivity, abundance and purity of desired eriodictyols available for commerce.

In addition to the above, while consumers approve and actively seek natural and biological sources for food, feed, flavor or medicinal components they are also concerned about sourcing, consistent taste profile and environmentally sustainable production. Into this situation, the microbial fermentation and production methods of the current invention provide the flavonoids of the invention in quantities useful for a variety of industries and research while doing so in a more natural fashion than inorganic synthesis or current plant extraction techniques.

Accordingly, a need exists for the development of a novel method of producing eriodictyol economically and conveniently to further enable human industrial use and consumption.

SUMMARY OF THE INVENTION

The present invention encompasses the method of producing eriodictyol from naringenin via modified *E. Coli* or other microbial strains.

In particular, the current invention provides for the production of eriodictyol via bioconversion.

The current method provides an approach for the biosynthesis of eriodictyol in microbial culture using a specific synthetic pathway.

In terms of product/commercial utility there are several products containing eriodictyol on the market in the United States and can be used in everything from analgesics to pest repellents as well as in foods and as a dietary supplement. Products containing eriodictyol can be aerosols, liquids, or granular formulations.

As for the cellular system in the embodiment, it is selected from the group consisting of bacteria, yeast, and a combination thereof, or any cellular system that would allow the genetic transformation with the selected genes and thereafter the biosynthetic production of eriodictyols from naringenin. In a most preferred microbial system, *E. coli* is used to produce eriodictyol and dihydroquercetin (("DHQ") or taxifolin).

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

BRIEF DESCRIPTION OF THE DRAWINGS

FIG. 4 shows sequence alignment of HpaC, PpFR and SeFR.

FIG. 6 shows relative enzymatic activity of the FAD reductases compared to HpaC activity.

FIG. 11 shows production of eriodictyol with the engineered strains of ERI-06, ERI-07 and ERI-08.

FIG. 12 shows the molecular structure of naringenin. $C_{15}H_{12}O_5$; average mass: 272.253 Da; naringenin—IUPAC name 5,7-dihydroxy-2-(4-hydroxyphenyl) chroman-4-one.

FIG. 13 shows the molecular structure of eriodictyol; $C_{15}H_{12}O_6$; average mass: 288.252 Da; eriodictyol—IUPAC name: (2S)-2-(3,4-dihydroxyphenyl)-5,7-dihydroxy-4-chromanone.

DESCRIPTION OF THE PREFERRED EMBODIMENT

Figure 1:
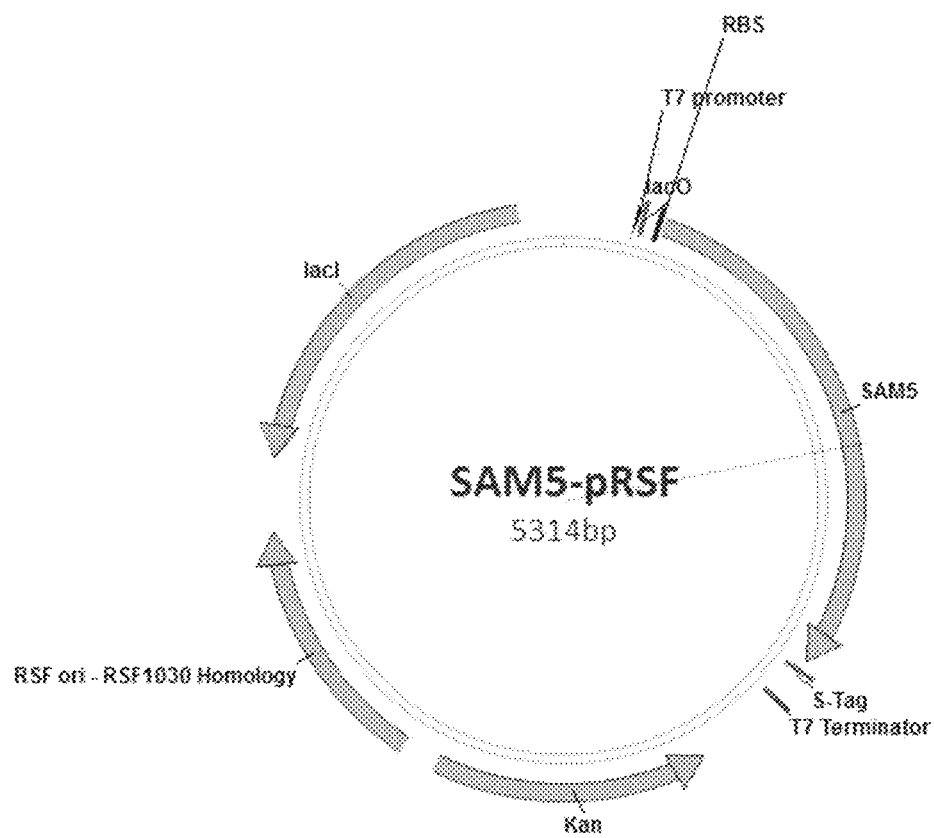
FIG. 1 shows the plasmid map of Sam5-pRSFDuet with key components.
Figure 2:
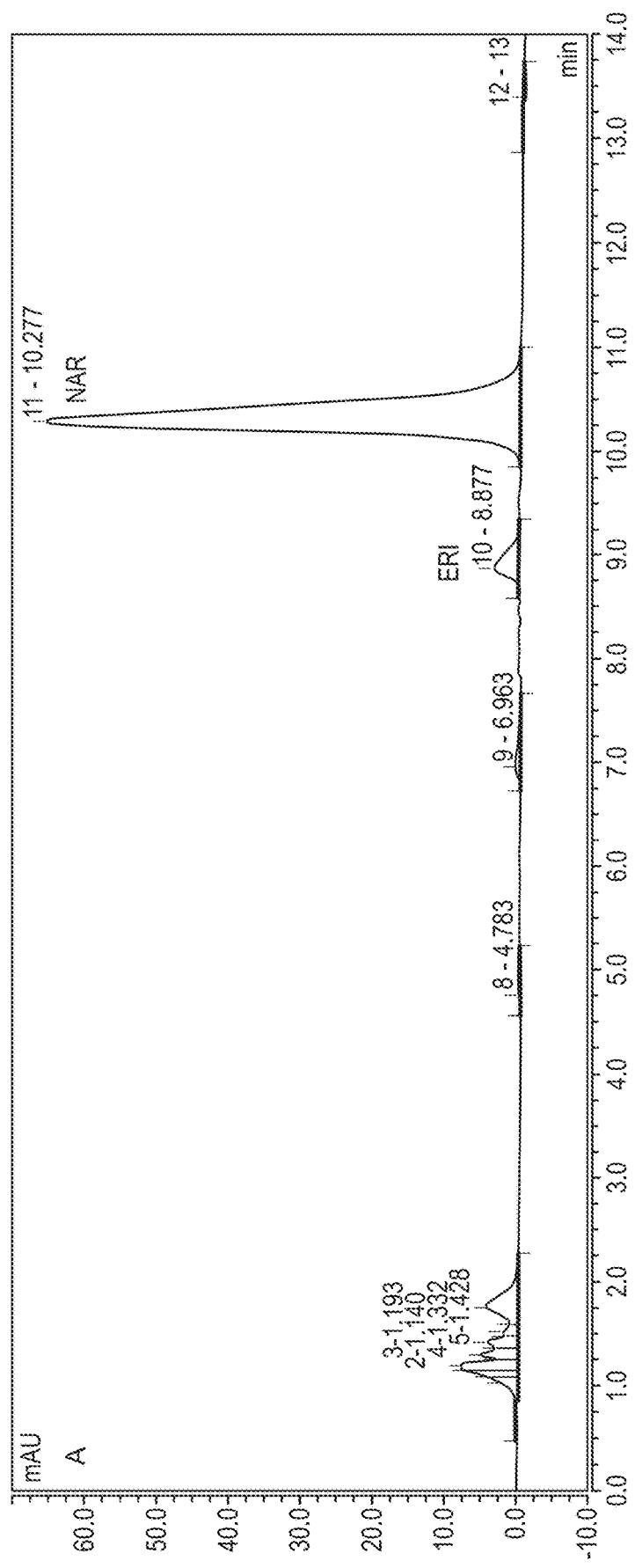
FIG. 2 shows HPLC analysis of the bioconversion of naringenin to eriodictyol with the strain ERI-01.
Figure 3A:
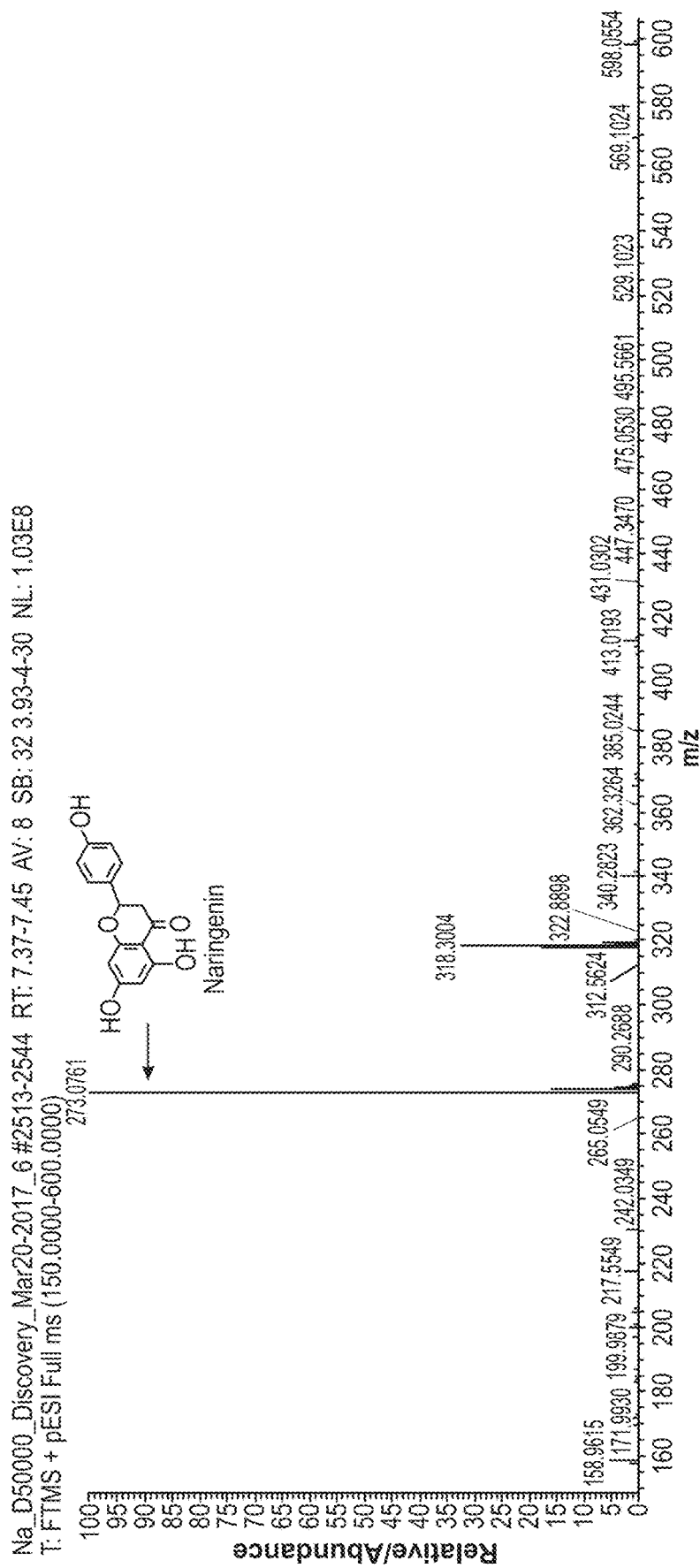
FIG. 3A shows LC-MS analysis of the bioconversion of naringenin with the strain ERI-01.
Figure 3B:
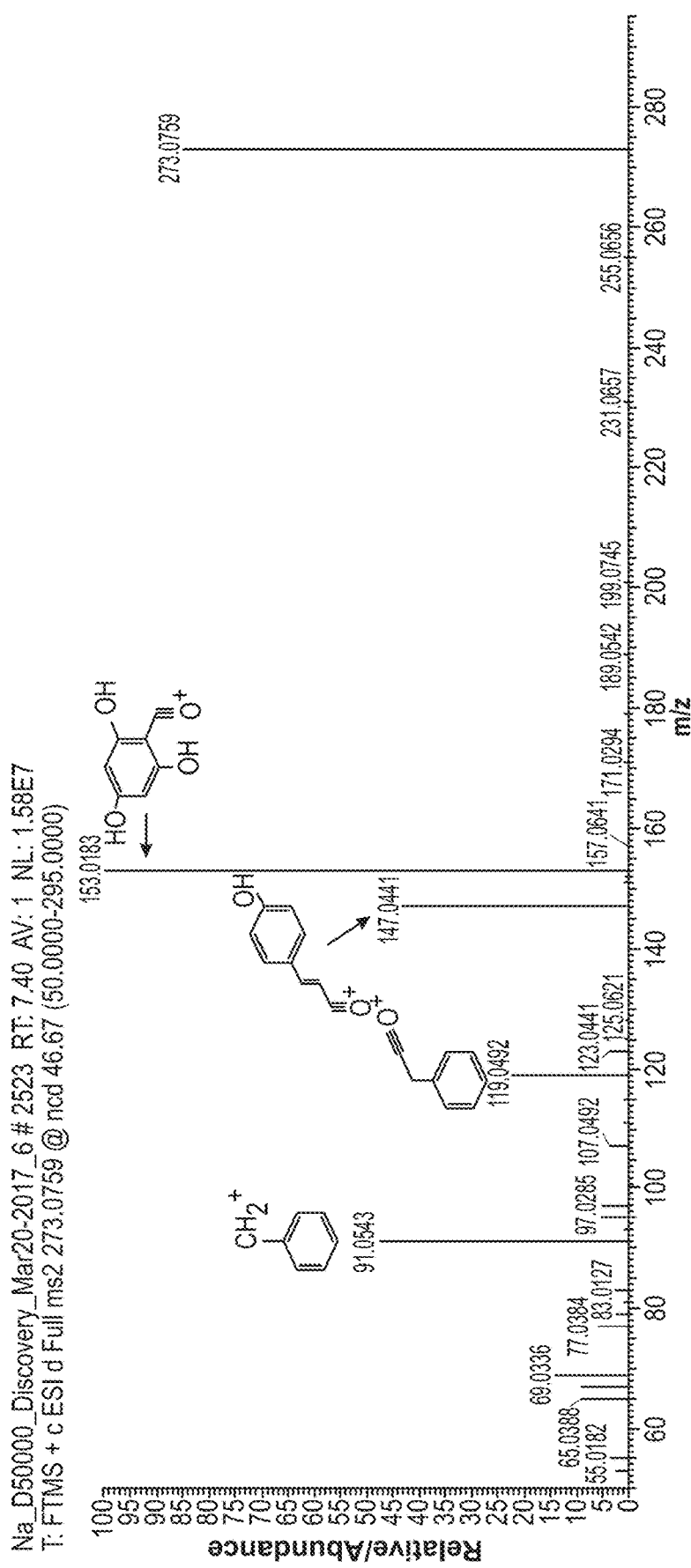
FIG. 3B shows LC-MS analysis of the bioconversion of naringenin with the strain ERI-01.
Figure 3C:
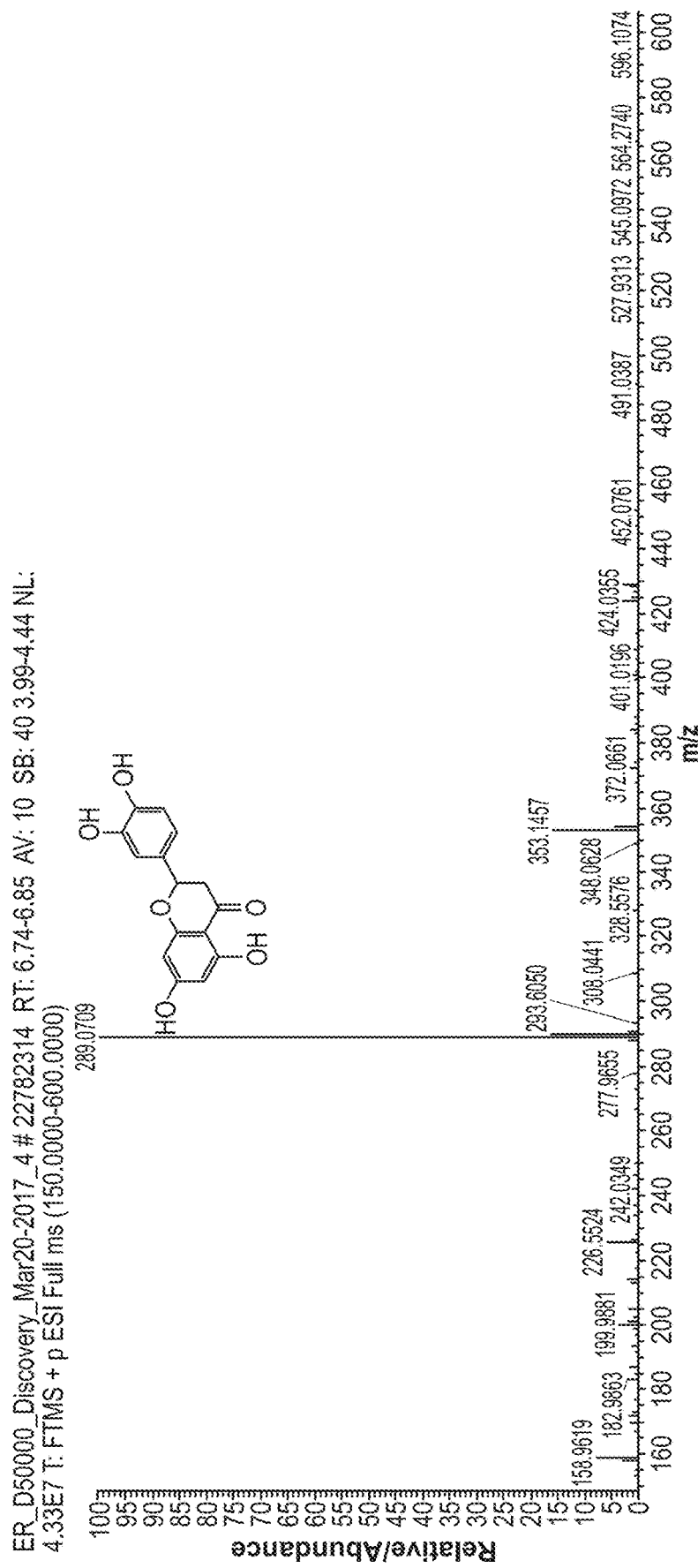
FIG. 3C shows LC-MS analysis of the bioconversion of naringenin with the strain ERI-01.
Figure 3D:
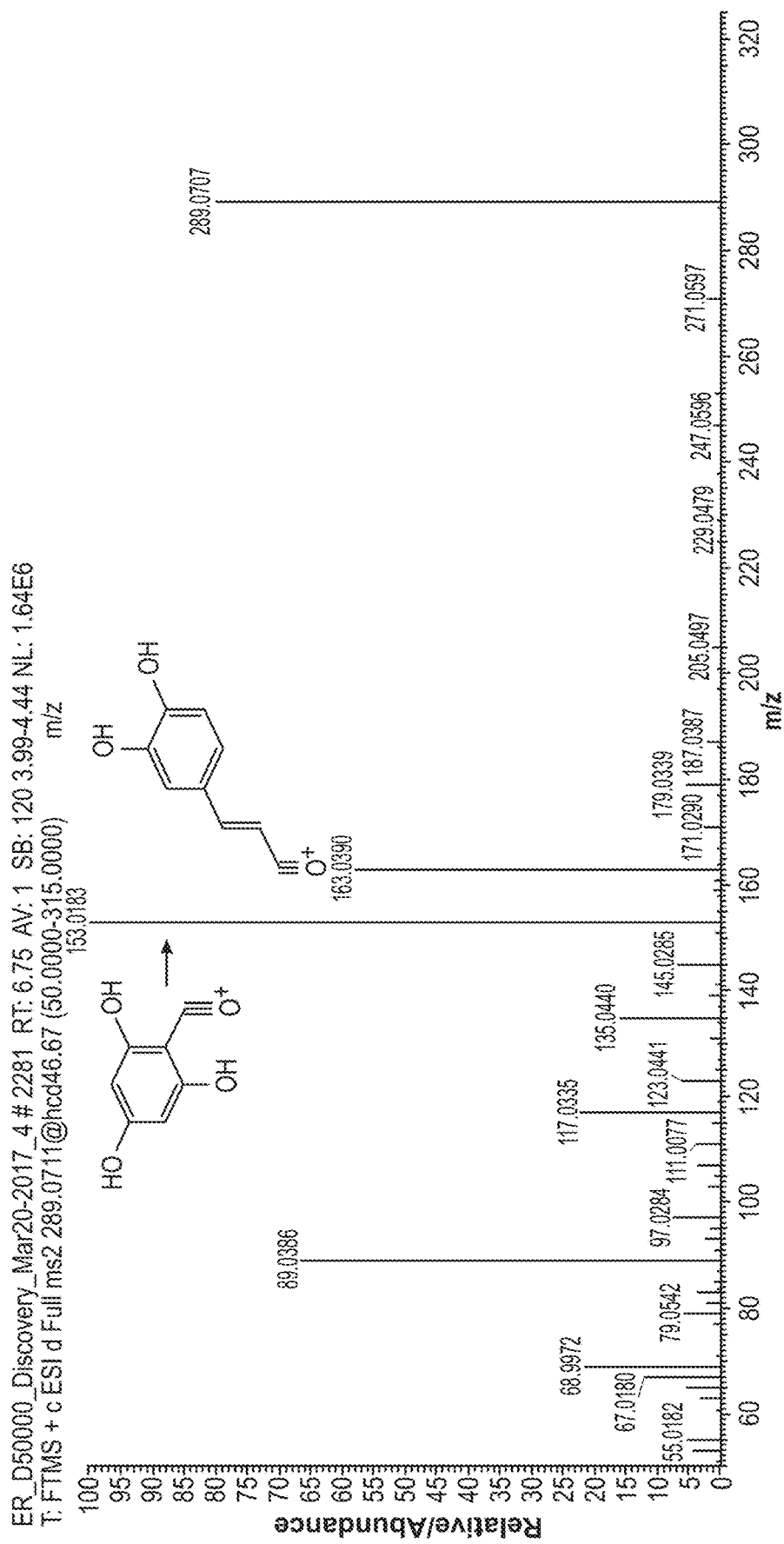
FIG. 3D shows LC-MS analysis of the bioconversion of naringenin with the strain ERI-01.

Explanation of Terms Used Herein:
Definitions:

Cellular system is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

"Coding sequence" is to be given its ordinary and customary meaning to a person of ordinary skill in the art, and is used without limitation to refer to a DNA sequence that encodes for a specific amino acid sequence.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Yeast. According to the current invention a yeast as claimed herein are eukaryotic, single-celled microorganisms classified as members of the fungus kingdom. Yeasts are unicellular organisms which evolved from multicellular ancestors but with some species useful for the current invention being those that have the ability to develop multicellular characteristics by forming strings of connected budding cells known as pseudo hyphae or false hyphae.

Structural Terms:

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

The term "complementary" is to be given its ordinary and customary meaning to a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences The terms "nucleic acid" and "nucleotide" are to be given their respective ordinary and customary meanings to a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing a eriodictyol composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are to be given their respective ordinary and customary meanings to a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full-length polypeptide or protein, and has substantially the same biological activity, or carries out substantially the same function as the full-length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90% at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art, and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments may be referred to as "transgenic."

The terms "transformed," "transgenic," and "recombinant," when used herein in connection with host cells, are to be given their respective ordinary and customary meanings to a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

DETAILED DESCRIPTION

Synthetic Biology

Standard recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. EXPERIMENTS WITH GENE FUSIONS; Cold Spring Harbor Laboratory: Cold Spring Harbor, N.Y., 1984; and by Ausubel, F. M. et al., IN CURRENT PROTOCOLS IN MOLECULAR BIOLOGY, published by Greene Publishing and Wiley-InterScience, 1987; (the entirety of each of which is hereby incorporated herein by reference).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these examples, while indicating preferred embodiments of the subject technology, are given by way of illustration only. From the above discussion and these examples, one skilled in the art can ascertain the essential characteristics of the subject technology, and without departing from the spirit and scope thereof, can make various changes and modifications of the subject technology to adapt it to various uses and conditions.

Materials and Methods

Bacterial Strains, Plasmids and Culture Conditions.

*E. coli* strains of DH5a and BL21 (DE3) were purchased from Invitrogen and the plasmid pRSFDuet-1 and pCDF-Duet-1 were purchased from Novagen for DNA cloning and recombinant protein expression purposes.

DNA Manipulation.

All DNA manipulations were performed according to standard procedures. Restriction enzymes and T4 DNA ligase were purchased from New England Biolabs. All PCR reactions were performed with New England Biolabs' Phusion PCR system according to the manufacturer's guidance.

Identification of Target Genes

SAM5, a 4-coumarate 3-hydroxylase from *Saccharothrix espanaensis* with a NCBI Reference Sequence ID of WP_015103234.1, was first functionally characterized to catalyze the meta-hydroxylation of p-coumaric acid to caffeic acid (Berner et al. 2006). Its corresponding nucleotide was synthesized in GenScript Company after codon optimization for expression in *Escherichia coli* (Seq ID NO. 1). To identify potentially interesting flavin reductase genes, key words "flavin reductase" was used to search for proteins in *Pseudomonas fluorescence* Pf-5 and *Saccharothrix espanaensis* in NCBI database, which yielded two homologs PfFR and SeFR with the GenBank ID of AAY92875.1 and NCBI Reference Sequence of WP_041313262, respectively. Their corresponding nucleotide sequences were generated with the codon optimized for expression in *Escherichia coli* and synthesized in Genscript (NJ). HpaC, encoding a flavin reductase, a component of 4-hydroxyphenylacetic hydroxylase complex in *E. coli* (Galan et al. 2000) that was also included in this study.

Construction of Plasmids.

The DNA fragments of Sam5 and two uncharacterized flavin reductases, PpFR and SeFR, were codon optimized for *E. coli* expression with the sequences listed in Seq ID NO.1, Seq ID NO.3, and Seq ID NO.5, respectively. Native HpaC DNA sequence is listed in Seq ID NO.7. Their corresponding protein sequences are listed in Seq ID NO.2, Seq ID NO.4, Seq ID NO.6 and Seq ID NO.8, respectively. Sam5, PpFR and SeFR were synthesized in Genscript Company and used as the templates for the following PCR amplification.

Sam5 was cloned into the Nde I/Xho I restriction site of pRSFDuet-1. PpFR, SeFR and HpaC were cloned into the Nde I/Xho I restriction sites of pCDFDuet-1. For enzyme overexpression and purification, HpaC, PpFR and SeFR were cloned into Nde I/Xho I restriction site of pET28a vector.

HpaC was cloned from genomic DNA of *E. coli* strain MG1655 was extracted using Bacterial DNA extraction kit. HpaC gene was amplified from the *E. coli* genomic DNA with PCR with introduction of Nde I site at the 5'-end and Xho I site at the end of 3'-end. The primers used were forward primer HpaC_NdeI_F (5'-GGGAATTC-CATATGCAATTAGATGAACAACGCCTGCG) and reverse primer HpaC_XhoI_R (5'-CTCGAGCGGT-TAAATCGCAGCTTCCATTTCCAGC). The PCR product digested with Nde I and Xho I was ligated with plasmid pCDFDuet-1 digested with the same enzymes and transformed into *E. coli* DH5a. The plasmid, HpaC-pCDF, extracted from the colony with the positive insert and confirmed by sequencing.

To make constructs with an operon of SAM5 and a specific flavin reductase, the specific flavin reductase gene was insert downstream of SAM5 by Gibson assembly, yielding three constructs named SAM5-HpaC-pRSF, SAM5-PpFR-pRSF and SAM5-SeFR-pRSF.

Transformation of *E. coli* BL21 (DE3) with the Developed Constructs.

Sam5-pRSF was introduced into *E. coli* BL21 (DE3) cells with standard chemical transformation protocol, leading to the development of eriodictyol producing *E. coli* strains, named as ERI-01. Sam5-pRSF was co-transformed into BL21 (DE3) with PCDFDuet-1, PpFR-pCDF, SeFR-pCDF and HpaC-pCDF respectively according to the standard procedure, generating corresponding eriodictyol producing *E. coli* strains ERI-02, ERI-03, ERI-04 and ERI-05. The three plasmids with the constructed operon, SAM5-HpaC-pRSF, SAM5-PpFR-pRSF, and SAM5-SeFR-pRSF, was transformed into BL21(DE3) respectively, yielding three *E. coli* strains, ERI-06, ERI-07 and ERI-08.

Overexpression and Purification of HpaC, PpFR and SeFR in *E. coli*

The plasmids, HpaC-pET28a, PpFR-pET28a and SeFR-pET28a, were transformed into BL21(DE3) competent cells for heterologous protein expression with standard procedure, respectively. A single colony for each transformation was grown in 5 mL of LB medium with 50 mg/L of kanamycin at 37° C. until OD600 reached about 1.0, and these seed cultures were transferred to 200 mL of LB medium with 50 mg/L of kanamycin. The cells were grown at 37° C. at 250 rpm to OD600 of 0.6-0.8, and then IPTG was added to a final concentration of 0.5 mM and the growth temperature was changed to 16° C. The *E. coli* cells were harvested after 16 hours of IPTG induction for protein purification by centrifugation at 4000 g for 15 min at 4 C. The resultant pellet was re-suspended in 5 mL of 100 mM Tris-HCl, pH 7.4, 100 mM NaOH, 10% glycerol (v/v), and sonicated for 2 min on ice. The mixture was centrifuged at 4000 g for 20 min at 4 C. The recombination protein in the supernatant was purified with His60 Ni Superflow resin from Clontech Inc. per the manufacturer's protocol.

Flavin Reductase Activity Measurement flavin reductase activity was determined by measuring the change of the absorbance at 340 nm at 30° C., using SpectraMax i3. Fixed amounts of purified proteins (0.1 μg, respectively) were incubated with 400 μM NADH and 200 μM FAD in reaction buffer (Tris-HCl 20 mM pH 7.4, final volume 100 μL). Assay mixtures without FAD were used as blanks.

Bioconversion of Naringenin to Eriodictyol

According to the current invention we have developed a system that overexpresses the flavin reductase together with SAM5 allowing the modified microbial strain of the current invention to catalyze the conversion of naringenin to eriodictyol with high efficiency. The titer in the shaking flask reached to 0.65 g/L in 6 hours. The microbial system utilize were *E. Coli* BL21(DE3) strains ERI-01, ERI-06, ERI-07, ERI-08 and pRSF-BLK were grown in LB medium with 30n/L kanamycin; ERI-02, ERI-03, ERI-04, and ERI-05 were grown in LB medium containing 30 μg/L kanamycin and 100 μg/L spectinomycin respectively. The cells were grown to OD600=0.6 in a shaker at 37° C., and then changed to 30° C. with addition of lactose to final concentration of 1.5% (w/v) to induce the expression of exogenous genes. After 3 hours of expression induction, naringenin (40% w/v)

dissolved in DMSO was added to the culture. The culture was kept shaking under the same culture condition. Samples were taken at 6 hours after substrate feeding for HPLC analysis.

HPLC and LC-MS Analysis.

The HPLC analysis of flavonoids was carried out with Dionex Ultimate 3000 system. Intermediates were separated by reverse-phase chromatography on a Dionex Acclaim 120 C18 column (particle size 3 mm; 150 by 2.1 mm) with a gradient of 0.15% (vol/vol) acetic acid (eluant A) and acetonitrile (eluant B) in a range of 10 to 40% (vol/vol) eluant B and at a flow rate of 0.6 ml/min. For quantification, all intermediates were calibrated with external standards. The compounds were identified by their retention times, as well as the corresponding spectra, which were identified with a diode array detector in the system.

E. coli strains of DH5a and BL21 (DE3) were purchased from Invitrogen and the plasmid pRSFDuet-1 and pCDF-Duet-1 were purchased from Novagen for DNA cloning and recombinant protein expression purposes.

Production Systems

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR). In molecular cloning, a vector is a DNA molecule used as a vehicle to artificially carry foreign genetic material into another cell, where it can be replicated and/or expressed (e.g.—plasmid, cosmid, Lambda phages). A vector containing foreign DNA is considered recombinant DNA. The four major types of vectors are plasmids, viral vectors, cosmids, and artificial chromosomes. Of these, the most commonly used vectors are plasmids. Common to all engineered vectors are an origin of replication, a multicloning site, and a selectable marker.

A number of molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerizing activities, thereby generating blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, NUCL. ACID. RES. 18 6069-74, (1990), Haun, et al, BIOTECHNIQUES 13, 515-18 (1992), each of which are incorporated herein by reference).

In an embodiment, in order to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared using PCR appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector, In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a *petunia* plant cell.

Microbial host cell expression systems and expression vectors containing regulatory sequences that direct high-level expression of foreign proteins that are well-known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Termination control regions may also be derived from various genes native to the microbial hosts. A termination site optionally may be included for the microbial hosts described herein.

Biosynthesis and Use of the Flavonoids of the Invention

One with skill in the art will recognize that the eriodictyol composition produced by the method described herein can be further purified and mixed with other, dietary supplements, medical compositions, cosmeceuticals, for nutrition, as well as in pharmaceutical products.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity genes of the current invention are capable of directing the production eriodictyol and have a substantial percent sequence identity to the polynucleotide sequences provided herein and are encompassed within the scope of this invention.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples provided herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Results

Sam5 Activity in the Bioconversion of Naringenin to Eriodictyol

As shown in FIG. 1, Sam5 was inserted into the second poly cloning site of pRSFDuet-1. The gene expression is under the control of T7 promoter. When plasmid Sam5-pRSF was introduced into BL21(DE3), the cells had the ability to convert naringenin fed in the culture to eriodictyol, while no eriodictyol was produced in the control strain ERI-Ctrl harboring pRSFDuet-1 plasmid without Sam5. As shown in the HPLC profile, there was a new compound with a little amount produced after naringenin was fed in the cell culture. The retention time of this compound in HPLC analysis and the absorption spectrum are corresponding to eriodictyol. Further analysis of the peaks separated by HPLC confirmed the bioconversion of naringenin to eriodictyol, as shown in FIGS. 3A-3D.

PpFR and SeFR are Flavin Reductases.

Figure 5:
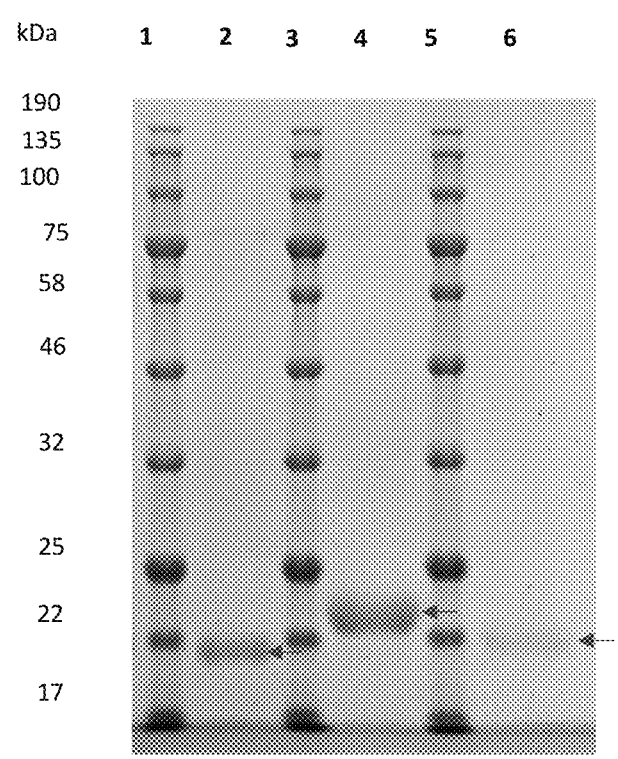
FIG. 5 shows SDS-PAGE of purified flavin reductase. Lanes 1, 3, and 5 are protein markers with the corresponding sizes listed on the left. Purified flavin reductases were indicated by the arrows. Lane 2: SeFR; Lane 4: PpFR and Lane 6: HpaC.
Figure 7A:
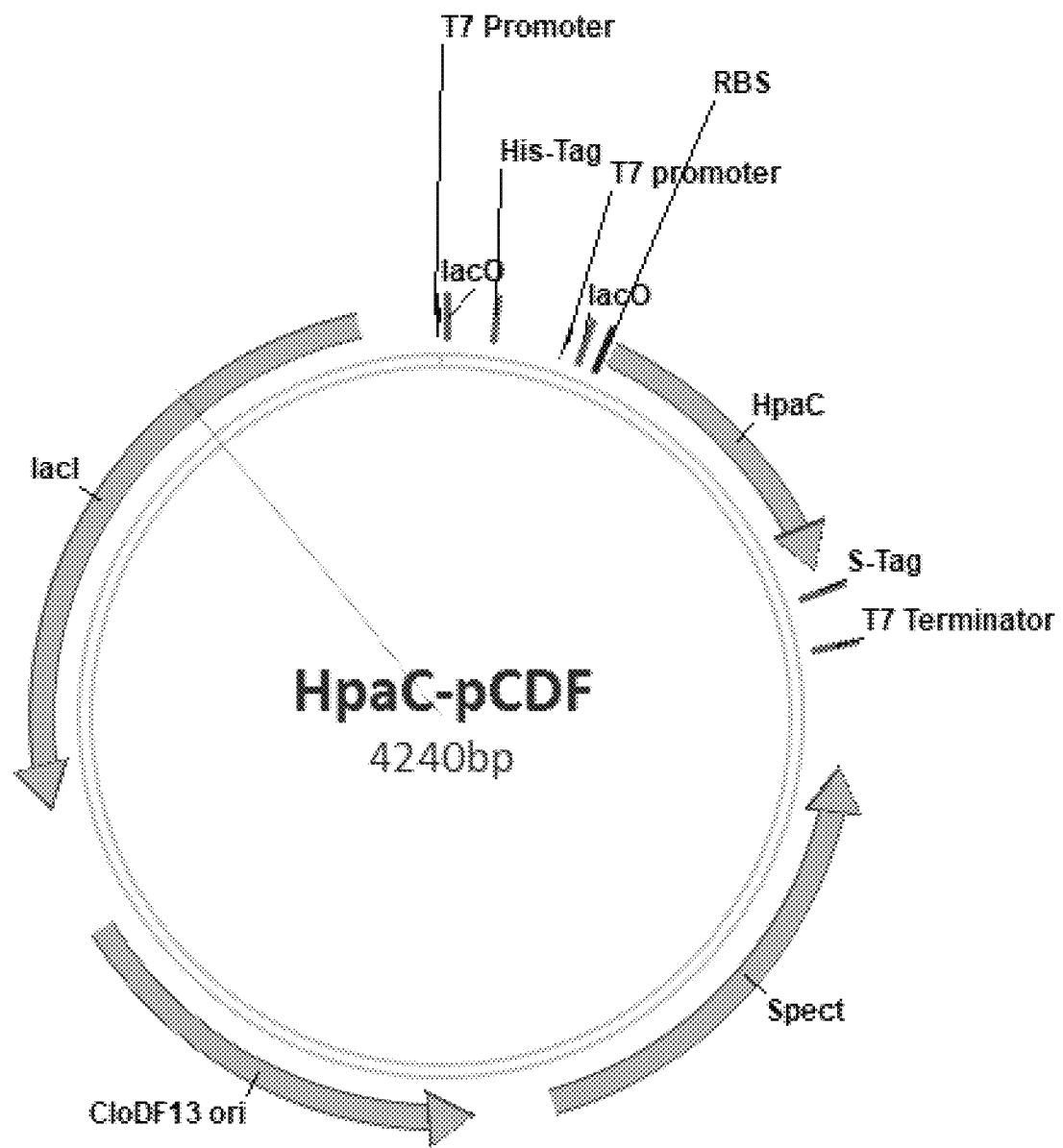
FIG. 7A is a map of plasmid HpaC-pCDF.
Figure 7B:
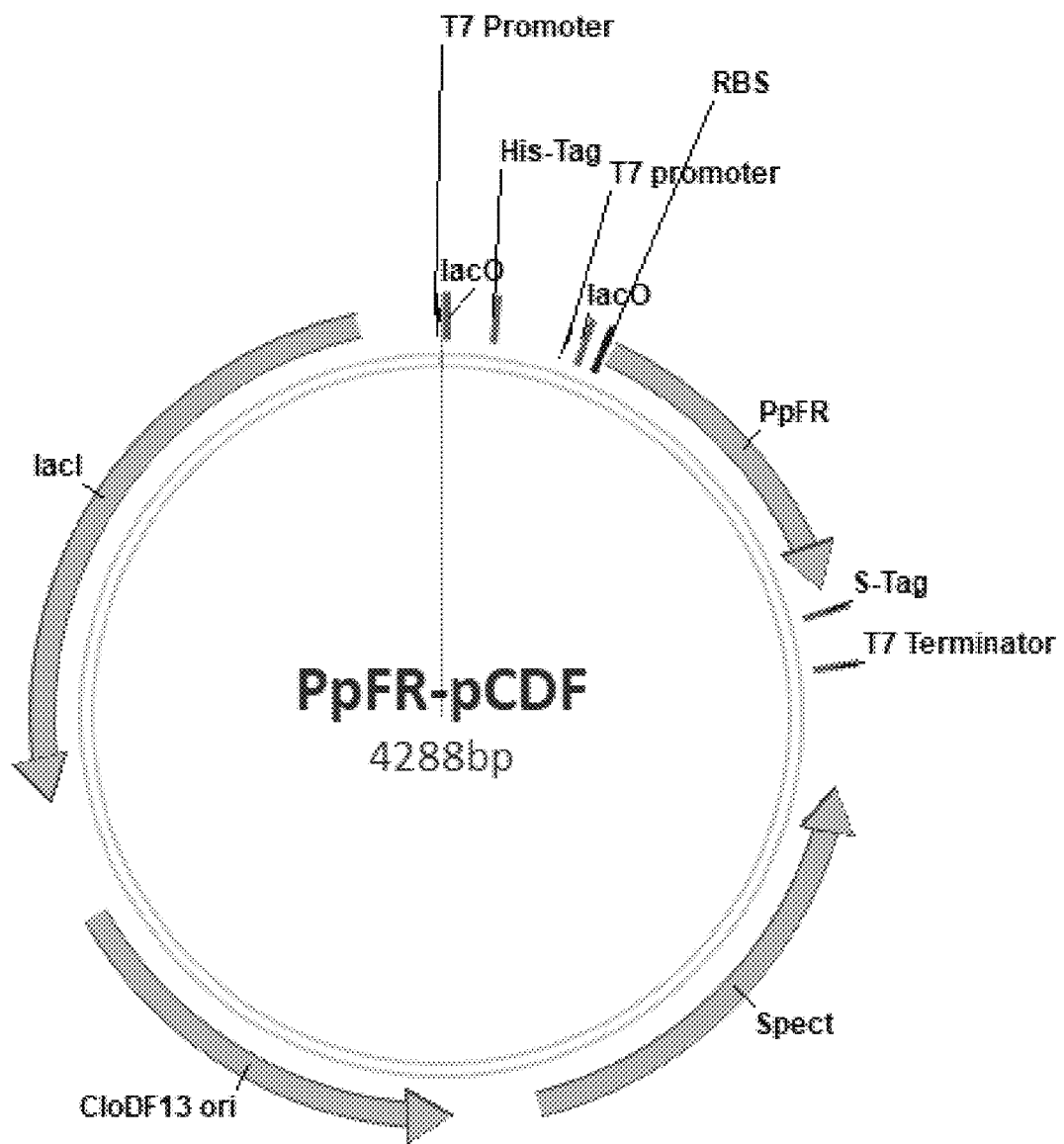
FIG. 7B is a map of plasmid PpFR-pCDF.
Figure 7C:
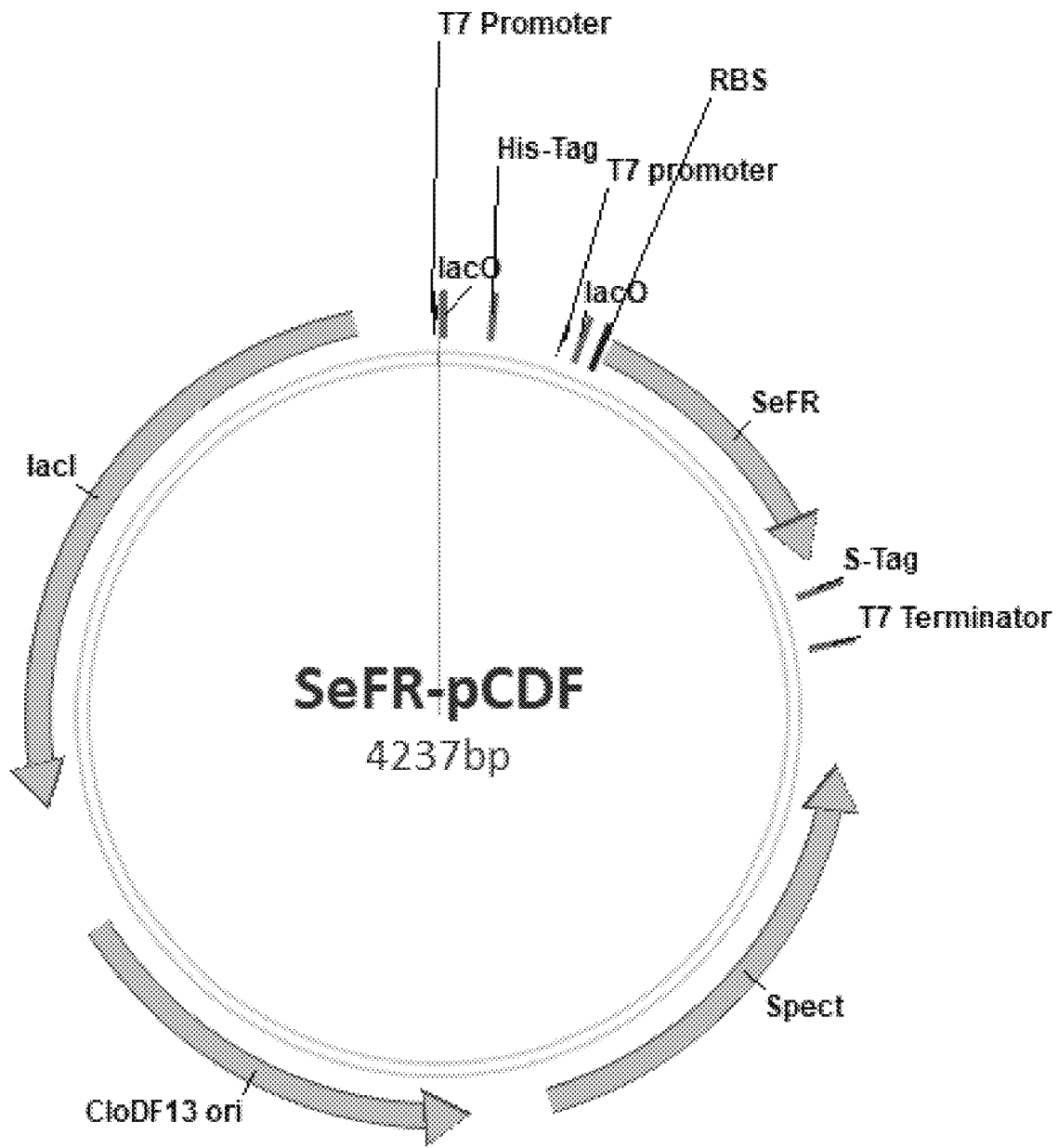
FIG. 7C is a map of plasmid SeFR-pCDF

HpaC, encodes a flavin reductase, a component of 4-hydroxyphenylacetic hydroxylase complex in *E. coli* (Galan et al. 2000). Two other genes, PpFR and SeFR, were identified from NCBI database in our study. Sequence analysis shows both of them shares low identity with HpaC, which is 22.9% and 30.2%, respectively. However, each of these three proteins possess the S/T/CxxPP and DGH consensus motifs characteristic of the HpaC-like subfamily of the Class I flavin reductases (FIG. 4). Therefore, PpFR and seFR was annotated as a member of the HpaC-like subfamily of the Class I flavin reductases (Van Lanen et al. 2009). All these three genes were cloned into pET28a vector respectively (FIGS. 7A-7C), and introduced into *E. coli* BL21 (DE3) for overexpression. The recombinant proteins were expressed in *E. coli* and purified to homogeneity (FIG. 5) for biochemical analysis. The results clearly confirmed the above bioinformatics analysis. As HpaC does, PpFR and SeFR catalyze the reduction of FAD with NADH and the specific activities of PpFR and SeFR are comparable to that of HpaC (FIG. 6).

Flavin Reductase Dramatically Increases the Bioconversion of Naringenin to Eriodictyol by Sam5.

Figure 8:
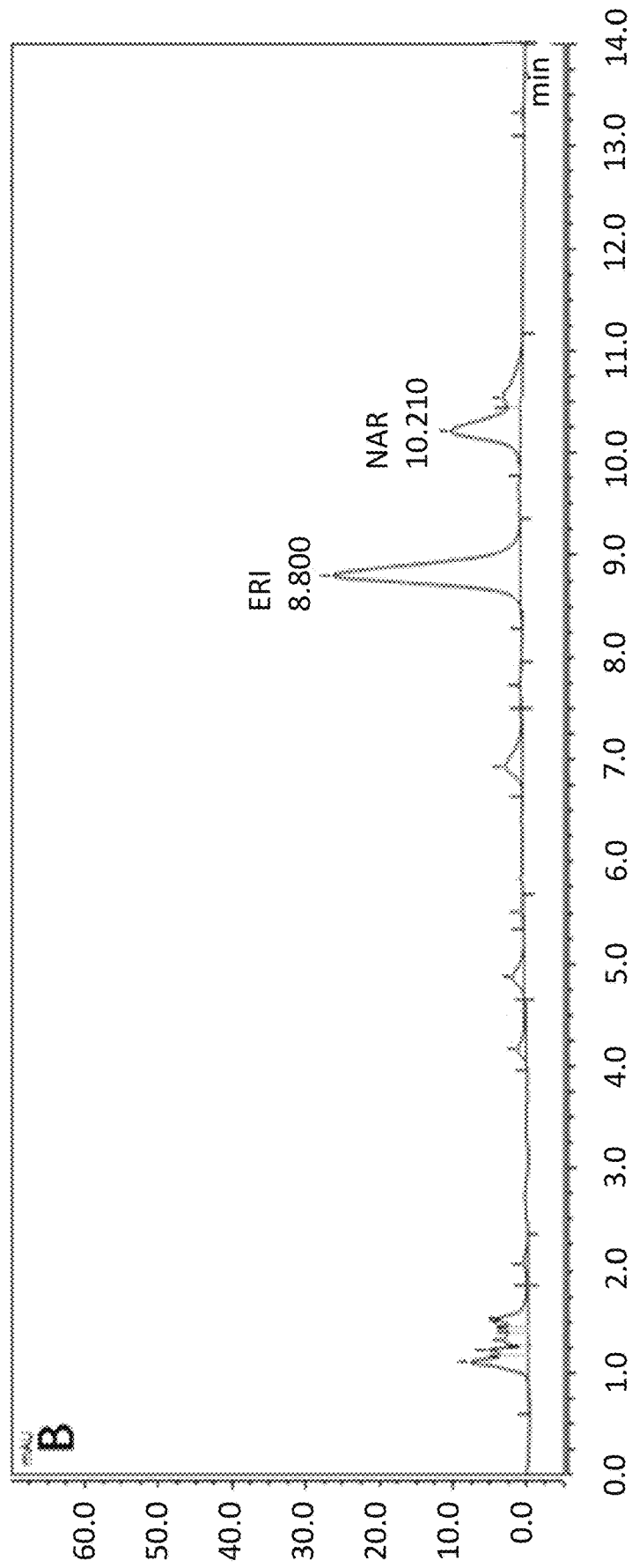
FIG. 8 shows production of eriodictyol in strain ERI-03 as measured by HPLC.
Figure 9:
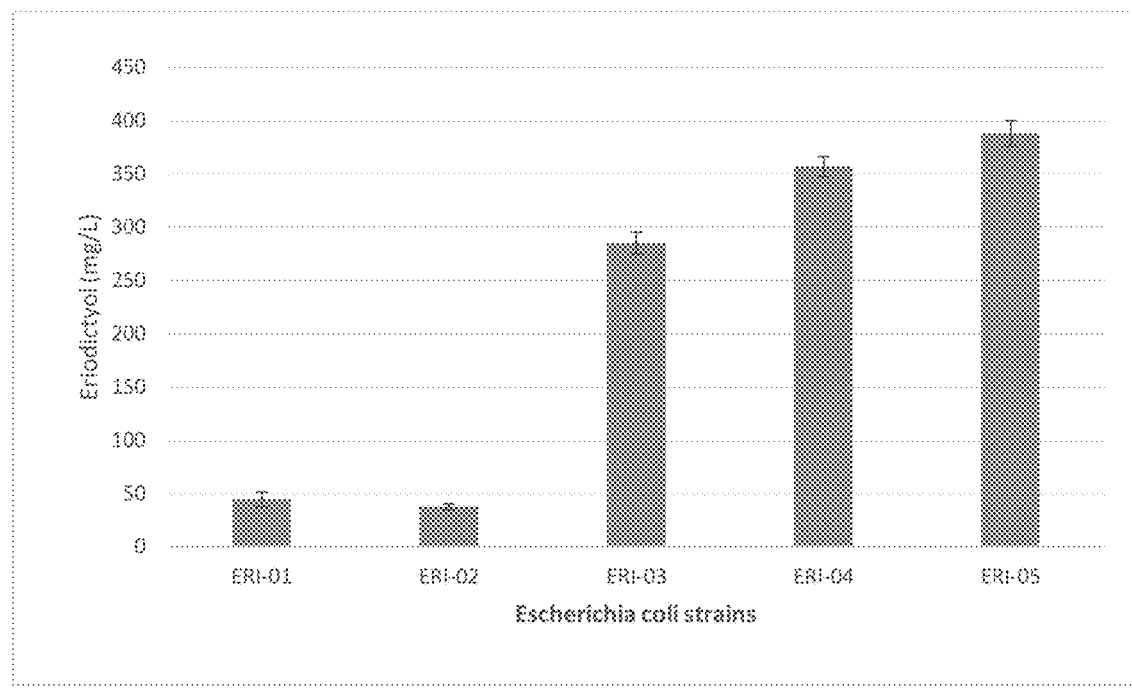
FIG. 9 shows production of eriodictyol each of the strains ERI-01, ERI-02, ERI-03, ERI-04, and ERI-05.
Figure 10A:
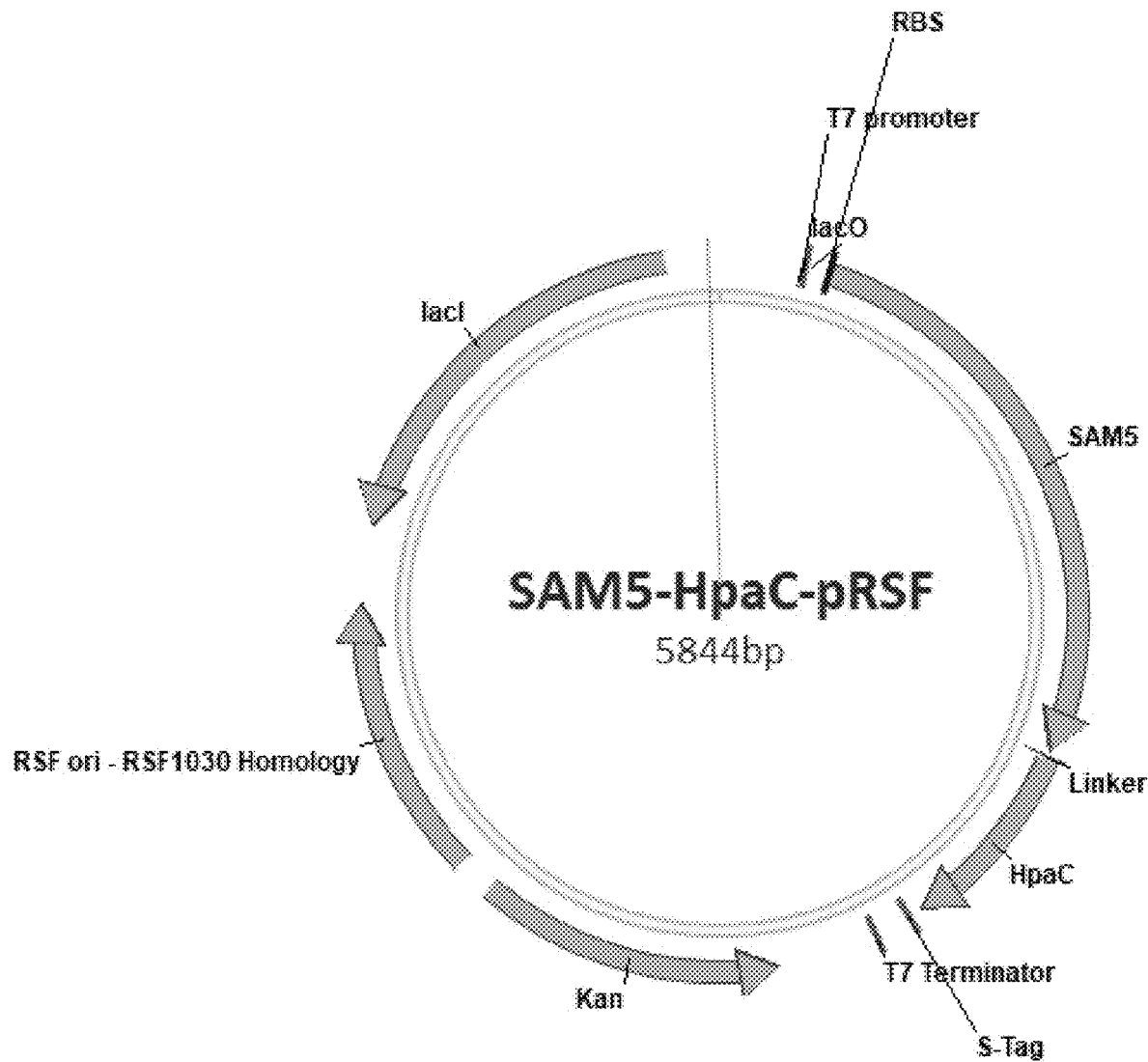
FIG. 10A shows the plasmid map containing the isolated flavin reductase HpaC.
Figure 10B:
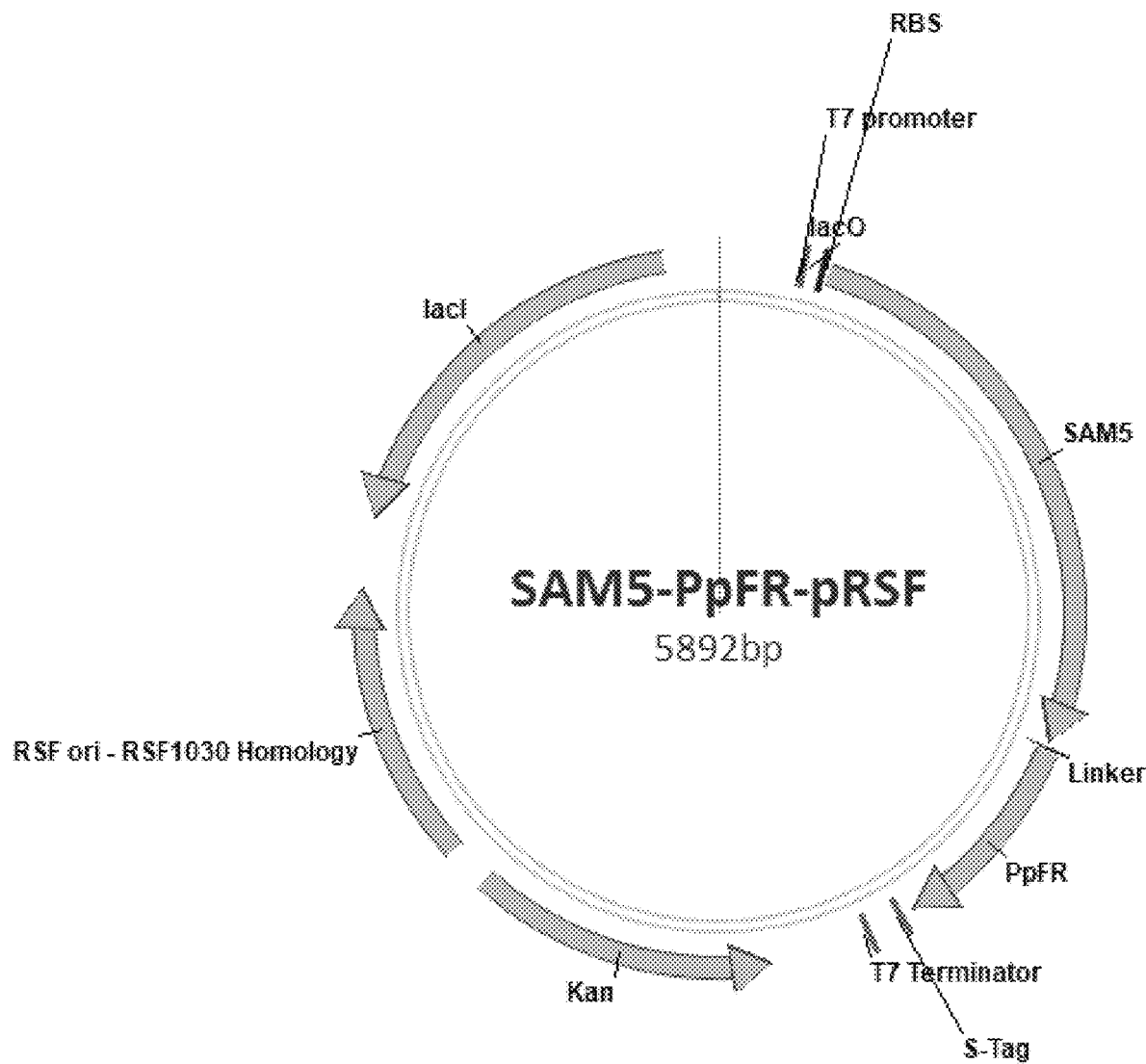
FIG. 10B shows the plasmid map containing the isolated flavin reductase PpFR
Figure 10C:
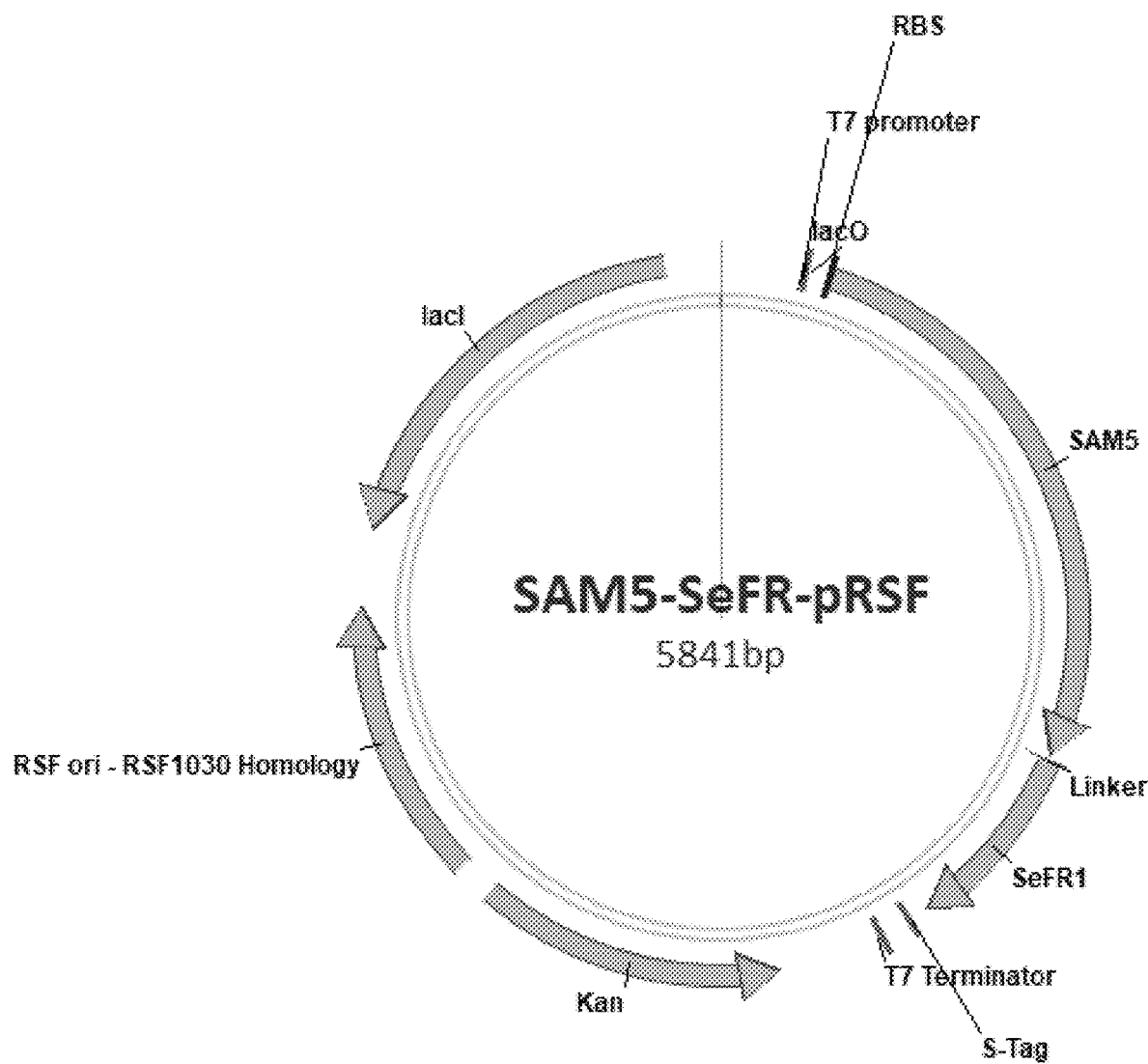
FIG. 10C shows the plasmid map containing the isolated flavin reductase SeFR

When HpaC-pCDF was co-expressed with Sam5-pRSF in *E. coli* cells, the resultant engineered cells ERI-03 can convert naringenin to eriodictyol with much higher activity in vivo. As shown in FIG. 8, the produced eriodictyol was at a much higher level compared to that produced by SAM5 alone. The eriodictyol production with ERI-03 strain reached 0.285 g/L in 6 hours, which are 6.3-fold and 7.5-fold increases compared to those with the ERI-01 and ERI-02 strains respectively (FIG. 9). PpFR and SeFR showed the stimulatory effect on SAM5 as well. ERI-04 and ERI-05 were shown to possess high activity to catalyze the hydroxylation of naringenin to produce eriodictyol. As shown in FIG. 9, eriodictyol accumulated to 357 mg/L and 388 mg/L in the cell culture in 6 hours after feeding naringenin in ERI-04 and ERI-05 respectively. In comparison with that of ERI-03, the titer of eriodictyol produced by ERI-04 and ERI-05 increased by 25% and 36%, respectively (FIG. 9). This result suggests PpFR and SeFR might be more effective in facilitating the hydroxylation of naringenin catalyzed by Sam5.

The Operon of SAM5 and Flavin Reductase Further Increased the Bioconversion of Naringenin to Eriodictyol As shown in FIG. 9, the produced eriodictyol with strain ERI-02 was lower than that with ERI-01, which may be caused by two antibodies used by the co-expression strain. SAM5 and a flavin reductase was constructed to an operon in an expression vector (FIG. 9). The resultant *Escherichia coli* strains ERI-06, ERI07 and ERI-08 were tested for the bioconversion of naringenin to eriodictyol. As shown in FIG. 11, the titers reached to 589, 614 and 638 mg/L, significantly higher than the corresponding co-expression strains.

Cosmoceutical & Supplement Use

Molecular biology plays a pivotal role in innovating cosmoceuticals. Compound identification now begins with the identification of molecular targets. For example, the importance of free radicals in association with skin aging has led in recent years to an intensive search for active substances which eliminate the harmful effects of free radicals and thus protect the tissue from oxidative damage. Skin aging manifests as age spots, more specifically as melasma, dyschromia, melanomas, and wrinkling, mainly attributed to free radical damage to the tissues that triggers cross linking and glycation of structural proteins, and pro-inflammatory enzyme systems. The use of flavonoids in cosmetics or pharmacy is known per se. Natural antioxidants, such as the eriodictyol of the invention, that quench free radicals are an essential component of anti-ageing formulations. They potentially offer protection against damage to the tissues, and against the detrimental effects of environmental and other agents. Biochemical reactions that accelerate the progression of skin ageing have their roots in inflammatory processes, as inflammation generates microscars that develop into blemishes or wrinkles.

These flavones and flavone glycoside derivatives (flavonoids) discussed herein are known to be scavengers of oxygen radicals and inhibitors of skin proteases so that they are actively able to counteract the aging of the skin and scar formation. By virtue of their coloring properties, some flavones, such as quercetin, are also useful as food colorants. At the same time, their ability to trap oxygen radicals also enables them to be used as antioxidants. Some flavonoids are inhibitors of aldose reductase which plays a key role in the formation of diabetes damage (ex: vascular damage). Other flavonoids (such as hesperidin and rutin) are used therapeutically, more particularly as vasodilating capillary-active agents.

Scientific research has confirmed a wide influence of flavonoid compounds on various levels of the skin. The uppermost layer of the skin, the stratum corneum, is a structure very rich in lipids and other easily oxidizable compounds. In this layer flavonoids can play an efficient role as anti-oxidizing agents and free radical scavengers. Their antioxidant properties enable them to influence deeper, epidermal skin layers, preventing UV radiation damage and inhibiting some enzyme functions. In the dermis, the deepest skin layer, flavonoids influence the permeability and fragility of the micro-vessel system. The valuable features of flavonoids described already makes them valuable for the cosmetic industry.

STATEMENT OF INDUSTRIAL APPLICABILITY/TECHNICAL FIELD

This disclosure has applicability in the food, feed, cosmoceutical, and pharmacological industries. This disclosure relates generally to a method for the biosynthetic production of eriodictyol via a modified microbial strain.

LITERATURE CITED AND INCORPORATED BY REFERENCE

1. Amor I L et al., (2010) *Biotransformation of naringenin to eriodictyol by Saccharomyces cerevisiae functionally expressing flavonoid 3' hydroxylase.* NAT PROD COMMUN. 5:1893-8.
2. Galan B., et al., (2000) *Functional analysis of the small component of the 4-hyroxylacetate 3-monooxygenase of Escherichia coli @: a prototype of a new Flavin: NAD (P)H reductase subfamily.* JOURNAL OF BACTERIOLOGY 182: 627-636.
3. Berner M, et al., (2006) *Genes and Enzymes Involved in Caffeic Acid Biosynthesis in the Actinomycete Saccharothrix espanaensis.* JOURNAL OF BACTERIOLOGY 188: 2666-2673.
4. Bravo L (1998) *Polyphenols: chemistry, dietary sources, metabolism, and nutritional significance.* NUTR REV 56:317-333.
5. Brugliera F., et al., (1999) *Isolation and characterization of a flavonoid 3'-hydroxylase cDNA clone corresponding to the Ht1 locus of Petunia hybrid.* PLANT J 19: 441-451.
6. Cao H, Chen X, Jassbi A R and Xiao J (2015) *Microbial biotransformation of bioactive flavonoids.* BIOTECHNOLOGY ADVANCES 33: 214-223.
7. Chu L L, et al., (2016) *Hydroxylation of diverse flavonoids by CYP450 BM3 variants: biosynthesis of eriodictyol from naringenin in whole cells and its biological activities.* MICROB CELL FACT. 15:135.
8. Du J et al., (2011), *Engineering microbial factories for synthesis of value-added products,* J IND MICROBIOL BIOTECHNOL. 38: 873-90.
9. Lee E R, Kim J H, Kang Y J, and Cho S G (2007) *The anti-apoptotic and anti-oxidant Effect of eriodictyol on UV-Induced apoptosis in keratinocytes.* BIOL PHARM BULL. 30: 32-37.
10. Lee H, Kim B G and Ahn J H (2014) *Production of bioactive hydroxyflavones by using monooxygenase from Saccharothrix espanaensis.* JOURNAL OF BIOTECHNOLOGY 176: 11-17.
11. Ley J P, Krammer G, Reinders G, Gatfield I L, and H J Bertram (2005) *Evaluation of bitter masking flavanones from Herba Santa (Eriodictyon californicum (H. & A.) Torr., Hydrophyllaceae).* J AGRI FOOD CHEM 53:6061-66.
12. Kaltenbach M, Schröder G, Schmelzer E, Lutz V, Schröder J. (1999), *Flavonoid hydroxylase from Catharanthus roseus: cDNA, heterologous expression, enzyme properties and cell-type specific expression in plants.* PLANT J. 19:183-93.
13. Kasai N., et al., (2009) *Enzymatic properties of cytochrome P450 catalyzing 3'-hydroxylation of naringenin from the white-rot fungus Phanerochaete chrysosporium,* BIOCHEM BIOPHYS RES COMMUN. 387:103-08.
14. Kim B G., et al., (2005). *Multiple regiospecific methylations of a flavonoid by plant O-methyltransferases expressed in E. coli.* BIOTECHNOL. LETT. 27: 1861-64.
15. Lamartiniere C A (2000) *Protection against breast cancer with genistein: a component of soy.* AM J CLIN NUTR 71:1705S-1707S.
16. Le Marchand L (2002) *Cancer preventive effects of flavonoids—a review.* BIOMED PHARMACOTHER 56:296-301.
17. Ley J. P. et al., *New Bitter-Masking Compounds: Hydroxylated Benzoic Acid Amides of Aromatic Amines as Structural Analogues of Homoeriodictyol,* J. AGRIC. FOOD CHEM., (2006) 54 (22): 8574-79.
18. Lim E-K., et al., (2004) *Arabidopsis glycosyltransferases as biocatalysts in fermentation for regioselective synthesis of diverse quercetin glucosides.* BIOTECHNOL. BIOENG. 87: 623-31.
19. Lin Y, Jain R and Yan Y (2014) *Microbial production of antioxidant food ingredients via metabolic engineering.* CURRENT OPINION IN BIOTECHNOLOGY 26: 71-78.
20. Lin Y and Yan Y (2014) *Biotechnological Production of Plant-Specific Hydroxylated Phenylpropanoids.* BIOTECHNOLOGY AND BIOENGINEERING 111:1895-1899.
21. Matsuo M, Sasaki N, Saga K, Kaneko T (2005) *Cytotoxicity of flavonoids toward cultured normal human cells.* BIOL PHARM BULL. 28 253-259.
22. Ogata S, Miyake Y, Yamamoto K, Okumura K, Taguchi H (2000) *Apoptosis induced by the flavonoid from lemon fruit (Citrus limon BURM. f.) and its metabolites in HL-60 cells.* BIOSCI BIOTECHNOL BIOCHEM 64: 1075-1078.
23. Steven G. Van Lanen, Shuangjun Lin, Geoff P. Horsman and Ben Shen (2009) *Characterization of SgcE6, the Flavin reductase component supporting FAD-dependent halogenation and hydroxylation in the biosynthesis of the enediyne antitumor antibiotic C-1027.* FEMS MICROBIOLOGY LETTER 300: 237-241.
24. Winkel-Shirley B (2001) *Flavonoid biosynthesis. A colorful model for genetics, biochemistry, cell biology, and biotechnology.* PLANT PHYSIOL. 126: 485-493.

Sequences of Interest

SEQ ID NO. 1: Nucleic Acid Sequence of SAM5
ATGACGATTACCTCTCCGGCCCCGGCTGGTCGCCTGAACAATGTGCGTCCGATGACGGGTGAA
GAATACCTGGAATCCCTGCGTGACGGTCGTGAAGTGTATATTTACGGCGAACGCGTCGATGAC
GTGACCACGCATCTGGCGTTCCGCAACAGCGTTCGTTCTATCGCCCGCCTGTATGATGTCCTGC
ACGATCCGGCCTCCGAAGGTGTTCTGCGCGTCCCGACCGATACCGGTAATGGTGGTTTTACCC
ATCCGTTTTTCAAAACGGCGCGTAGCTCTGAAGACCTGGTGGCGGCCCGTGAAGCCATTGTCG
GTTGGCAACGCCTGGTGTATGGCTGGATGGGTCGTACCCCGGATTACAAGGCAGCGTTTTTCG
GTACGCTGGACGCTAACGCGGAATTTTATGGCCCGTTCGAAGCCAATCACGTCGCTGGTATC
GTGATGCACAGGAACGCGTTCTGTACTTCAACCATGCTATCGTGCATCCGCCGGTCGATCGTG
ACCGTCCGGCTGATCGTACCGCCGACATTTGCGTCCATGTGGAAGAAGAAACGGATTCAGGCC
TGATCGTGTCGGGTGCCAAAGTGGTTGCAACCGGTTCTGCTATGACGAACGCGAATCTGATTG
CCCACTATGGTCTGCCGGTTCGCGATAAAAAGTTTGGCCTGGTGTTCACCGTTCCGATGAACA
GTCCGGGTCTGAAACTGATCTGTCGTACCTCCTATGAACTGATGGTGGCCACGCAGGGCTCAC

Sequences of Interest

CGTTTGATTACCCGCTGAGTTCCCGCCTGGATGAAAATGACAGCATTATGATCTTTGATCGTGT
TCTGGTCCCGTGGGAAAACGTTTTCATGTACGACGCAGGCGCGGCCAATAGCTTTGCTACCGG
CTCTGGTTTCCTGGAACGCTTTACCTTTCATGGCTGCACGCGTCTGGCAGTGAAACTGGATTTT
ATTGCAGGCTGTGTTATGAAGGCTGTGGAAGTTACCGGCACCACGCACTTCCGGTGTTCAG
GCGCAAGTCGGCGAAGTGCTGAACTGGCGTGATGTCTTTTGGGGTCTGTCGGACGCTATGGCG
AAAAGTCCGAACAGCTGGGTGGGCGGTAGCGTTCAGCCGAACCTGAATTATGGCCTGGCCTA
CCGCACCTTTATGGGCGTGGGTTATCCGCGTATTAAAGAAATTATCCAGCAAACGCTGGGCTC
TGGTCTGATCTACCTGAACTCATCGGCAGCTGATTGGAAGAATCCGGACGTTCGCCCGTATCT
GGATCGTTACCTGCGCGGCAGTCGTGGTATTCAGGCAATCGATCGTGTCAAACTGCTGAAGCT
GCTGTGGGACGCGGTGGGCACCGAATTTGCCGGTCGTCATGAACTGTATGAACGCAACTACG
GCGGTGATCACGAAGGCATTCGTGTGCAGACCCTGCAAGCCTATCAGGCAAATGGTCAAGCG
GCGGCACTGAAAGGCTTTGCGGAACAGTGCATGAGCGAATACGACCTGGATGGCTGGACCCG
CCCGGACCTGATTAACCCGGGCACCTGA

SEQ ID NO. 2 Amino Acid Sequence of SAM5
MTITSPAPAGRLNNVRPMTGEEYLESLRDGREVYIYGERVDDVTTHLAFRNSVRSIARLYDVLHDP
ASEGVLRVPTDTGNGGFTHPFFKTARSSEDLVAAREAIVGWQRLVYGWMGRTPDYKAAFFGTLD
ANAEFYGPFEANARRWYRDAQERVLYFNHAIVHPPVDRDRPADRTADICVHVEEETDSGLIVSGA
KVVATGSAMTNANLIAHYGLPVRDKKFGLVFTVPMNSPGLKLICRTSYELMVATQGSPFDYPLSS
RLDENDSIMIFDRVLVPWENVFMYDAGAANSFATGSGFLERFTFHGCTRLAVKLDFIAGCVMKAV
EVTGTTHFRGVQAQVGEVLNWRDVFWGLSDAMAKSPNSWVGGSVQPNLNYGLAYRTFMGVGY
PRIKEIIQQTLGSGLIYLNSSAADWKNPDVRPYLDRYLRGSRGIQAIDRVKLLKLLWDAVGTEFAG
RHELYERNYGGDHEGIRVQTLQAYQANGQAAALKGFAEQCMSEYDLDGWTRPDLINPGT.

SEQ ID NO. 3 Nucleic Acid Sequence of SeFR
ATGATGACCGTTTATGATAGCGCACTGACAATGGAAGAAACCACCCTGCGTGATGCAATGAG
CCGTTTTGCAACCGGTGTTAGCGTTGTTACCGTTGGTGGTGAACATACACATGGTATGACCGC
AAATGCCTTTACCTGTGTTAGCCTGGATCCGCCTCTGGTTCTGTGTTGTGTTGCACGTAAAGCA
ACCATGCATGCAGCAATTGAAGGTGCACGTCGTTTTGCAGTTAGCGTTATGGGTGGTGATCAA
GAACGTACCGCACGTTATTTTGCAGATAAACGTCGTCCGCGTGGTCGTGCACAGTTTGATGTT
GTTGATTGGCAGCCTGGTCCGCATACAGGTGCACCGCTGCTGAGCGGTGCGCTGGCATGGCTG
GAATGTGAAGTTGCACAGTGGCATGAAGGTGGCGATCATACCATTTTTCTGGGTCGTGTTCTG
GGTTGTCGTCGTGGTCCGGATAGTCCGGCACTGCTGTTTTATGGTAGCGATTTTCATCAGATCC
GCTAA SEQ ID NO. 4 Amino Acid Sequence of SeFR
MMTVYDSALTMEETTLRDAMSRFATGVSVVTVGGEHTHGMTANAFTCVSLDPPLVLCCVARKA
TMHAAIEGARRFAVSVMGGDQERTARYFADKRRPRGRAQFDVVDWQPGPHTGAPLLSGALAWL
ECEVAQWHEGGDHTIFLGRVLGCRRGPDSPALLFYGSDFHQIR.

SEQ ID NO. 5 Nucleic Acid Sequence of 5 PfFR
ATGAATGCAGCAACCGAAACCAAAGTTCATGATCTGCTGGATGCCGAAGGTCGTGATGTTCGT
GATGCACGTGAACTGCGTAATGTTCTGGGTCAGTTTGCAACCGGTGTTACCGTTATTACCACC
CGTACCGCAGATGGTCGTAATGTTGGTGTGACCGCAAATAGCTTTAGCAGCCTGAGCCTGAGT
CCGGCACTGGTTCTGTGGTCACTGGCACGTACCGCACCGAGCCTGAAAGTTTTTTGTAGCGCA
AGCCATTTTGCCATTAATGTGCTGGGTGCACATCAGCTGCATCTGAGCGAACAGTTTGCACGT
GCCGCAGCAGATAAATTTGCCGGTGTTGCACATAGTTATGGTAAAGCGGGTGCACCGGTTCTG
GATGATGTTGTTGCAGTTCTGGTTTGCCGTAATGTTACCCAGTATGAAGGTGGTGATCATCTGA
TTTTTATCGGCGAAATTGAGCAGTATCGTTATAGCGGTGCAGAACCGCTGGTTTTTCATGCAG
GTCAGTATCGTGGTCTGGGTAGCAATCGTGCAGAAAGCGTTCTGAAACATGAATAA SEQ ID NO. 6 Amino Acid Sequence of PfFR
MNAATETKVHDLLDAEGRDVRDARELRNVLGQFATGVTVITTRTADGRNVGVTANSFSSLSLSPA
LVLWSLARTAPSLKVFCSASHFAINVLGAHQLHLSEQFARAAADKFAGVAHSYGKAGAPVLDDV
VAVLVCRNVTQYEGGDHLIFIGEIEQYRYSGAEPLVFHAGQYRGLGSNRAESVLKHE.

SEQ ID NO. 7 Nucleic Acid Sequence of HpaC
ATGCAATTAGATGAACAACGCCTGCGCTTTCGTGACGCAATGGCCAGCCTGTCGGCAGCGGTA
AATATTATCACCACCGAGGGCGACGCCGGACAATGCGGGATTACGGCAACGGCCGTCTGCTC
GGTCACGGATACACCACCATCGCTGATGGTGTGCATTAACGCCAACAGTGCGATGAACCCGGT
TTTTCAGGGCAACGGTAAGTTGTGCGTCAACGTCCTCAACCATGAGCAGGAACTGATGGCACG
CCACTTCGCGGGCATGACAGGCATGGCGATGGAAGAGCGTTTTAGCCTCTCATGCTGGCAAAA
AGGTCCGCTGGCGCAGCCGGTGCTAAAAGGTTCGCTGGCCAGTCTTGAAGGTGAGATCCGCG
ATGTGCAGGCAATTGGCACACATCTGGTGTATCTGGTGGAGATTAAAAACATCATCCTCAGTG
CAGAAGGTCACGGACTTATCTACTTTAAACGCCGTTTCCATCCGGTGATGCTGGAAATGGAAG
CTGCGATTTAA SEQ ID NO. 8 Amino Acid Sequence of HpaC
MQLDEQRLRFRDAMASLSAAVNIITTEGDAGQCGITATAVCSVTDTPPSLMVCINANSAMNPVFQ
GNGKLCVNVLNHEQELMARHFAGMTGMAMEERFSLSCWQKGPLAQPVLKGSLASLEGEIRDVQ
AIGTHLVYLVEIKNIILSAEGHGLIYFKRRFHPVMLEMEAAI.

What is claimed is:

1. An isolated recombinant host cell transformed with:
   (i) a first nucleic acid comprising a polynucleotide sequence encoding a polypeptide comprising the amino acid sequence of SEQ ID NO: 2; and
   (ii) a second nucleic acid comprising a polynucleotide sequence encoding a Flavin reductase polypeptide comprising an amino acid sequence that is at least 95% identical to any one of SEQ ID NOs: 4, 6, and 8, wherein the flavin reductase directs the bioconversion of naringenin to a hydroxylated flavonoid.

2. The isolated recombinant cell of claim 1, wherein the second nucleic acid sequence comprises a polynucleotide sequence that is at least 95% identical to SEQ ID NO: 3.

3. The isolated recombinant call of claim 1, wherein the second nucleic acid comprises a polynucleotide sequence that is at least 95% identical to SEQ ID NO:5.

4. The isolated recombinant cell of claim 1, wherein the second nucleic acid comprises a polynucleotide sequence that is at least 95% identical to SEQ ID NO:7.

5. The isolated recombinant cell of claim 2, wherein the first nucleic acid comprises the polynucleotide of SEQ ID NO: 1.

6. The isolated recombinant cell of claim 2, wherein the second nucleic acid comprises the polynucleotide of SEQ ID NO: 3.

7. The isolated recombinant cell of claim 3, wherein the second nucleic acid comprises the polynucleotide of SEQ ID NO: 5.

8. The isolated recombinant cell of claim 4, wherein the second nucleic acid comprises the polynucleotide of SEQ ID NO: 7.

9. The isolated recombinant call of claim 1, wherein the polypeptide of (ii) comprises the amino acid sequence of SEQ ID NO: 4.

10. The isolated recombinant cell of claim 1, wherein the polypeptide of (ii) comprises the amino acid sequence of SEQ ID NO: 6.

11. The isolated recombinant cell of claim 1, wherein the polypeptide of (ii) comprises the amino acid sequence of SEQ ID NO: 8.

12. The isolated recombinant cell of claim 1, wherein the isolated recombinant cell is selected from the group consisting of: a bacteria, a yeast, a filamentous fungi, a cyanobacteria algae and a plant cell.

13. The isolated recombinant cell of claim 1, wherein the isolated recombinant cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Escherichia; Klebsiella; Pantoea; Salmonella Corynebacterium; Clostridium*; and *Clostridium acetobutylicum*.

14. A method of producing a hydroxylated flavonoid composition, the method comprising incubating the isolated recombinant host cell of claim 1 with the naringenin.

15. The method of claim 14, wherein the hydroxylated flavonoid composition comprises eriodictyol.

16. The isolated recombinant cell of claim 1 wherein the isolated recombinant cell is selected from the group consisting of: yeast, non-eriodictyol producing plants, algae and bacteria.

17. The isolated recombinant cell of claim 12 wherein the isolated recombinant cell is an *E. coli* cell.

18. The method of claim 15, wherein the isolated recombinant host cell is an *E. coli* cell.

19. The isolated recombinant cell of claim 1 wherein said isolated recombinant cell is a *Pichia Pastoris* cell.

20. The isolated recombinant cell of claim 1 wherein said isolated recombinant cell is a *Saccharomyces Cerevisiae* cell.

21. The method of claim 14, wherein the hydroxylated flavonoid composition comprises eriodictyol, pinocembrin, homoeriodictyol or a combination thereof.

22. The isolated recombinant cell of claim 1, wherein the first nucleic acid and the second nucleic acid are on two vectors.

23. The isolated recombinant cell of claim 1, wherein the first nucleic acid and the second nucleic acid are on the same vector.

24. The isolated recombinant cell of claim 1, wherein the polynucleotide sequence encoding the polypeptide of (i) is operably linked to one or more promoters.

25. The isolated recombinant cell of claim 1, wherein the polynucleotide sequence encoding the polypeptide of (ii) is operably linked to one or more promoters.

26. The method of claim 14, wherein the hydroxylated flavonoid composition comprises dihydroquercetin.

27. The isolated recombinant cell of claim 1, wherein the hydroxylated flavonoid is eriodictyol.

28. The isolated recombinant cell of claim 27, wherein the hydroxylated flavonoid is eriodictyol, pinocembrin, homoeriodictyol or a combination thereof.

29. The isolated recombinant cell of claim 1, wherein the hydroxylated flavonoid composition is dihydroquercetin.

* * * * *

SEQUENCE LISTING

<160> NUMBER OF SEQ ID NOS: 8

<210> SEQ ID NO 1
<211> LENGTH: 1539
<212> TYPE: DNA
<213> ORGANISM: Saccharothrix espanaensis

<400> SEQUENCE: 1

| | | |
|---|---|---|
| atgacgatta cctctccggc cccggctggt cgcctgaaca atgtgcgtcc gatgacgggt | 60 |
| gaagaatacc tggaatccct gcgtgacggt cgtgaagtgt atatttacgg cgaacgcgtc | 120 |
| gatgacgtga ccacgcatct ggcgttccgc aacagcgttc gttctatcgc ccgcctgtat | 180 |
| gatgtcctgc acgatccggc ctccgaaggt gttctgcgcg tcccgaccga taccggtaat | 240 |
| ggtggtttta cccatccgtt tttcaaaacg gcgcgtagct ctgaagacct ggtggcggcc | 300 |
| cgtgaagcca ttgtcggttg caacgcctg gtgtatggct ggatgggtcg taccccggat | 360 |
| tacaaggcag cgttttcgg tacgctggac gctaacgcgg aattttatgg cccgttcgaa | 420 |
| gccaatgcac gtcgctggta tcgtgatgca caggaacgcg ttctgtactt caaccatgct | 480 |
| atcgtgcatc cgccggtcga tcgtgaccgt ccggctgatc gtaccgccga catttgcgtc | 540 |
| catgtggaag aagaaacgga ttcaggcctg atcgtgtcgg gtgccaaagt ggttgcaacc | 600 |
| ggttctgcta tgacgaacgc gaatctgatt gcccactatg gtctgccggt cgcgataaa | 660 |
| aagtttggcc tggtgttcac cgttccgatg aacagtccgg gtctgaaact gatctgtcgt | 720 |
| acctcctatg aactgatggt ggccacgcag ggctcaccgt tgattaccc gctgagttcc | 780 |
| cgcctggatg aaaatgacag cattatgatc tttgatcgtg ttctggtccc gtgggaaaac | 840 |
| gttttcatgt acgacgcagg gcggccaat agctttgcta ccggctctgg tttcctggaa | 900 |
| cgctttacct tcatggctg cacgcgtctg gcagtgaaac tggattttat gcaggctgt | 960 |
| gttatgaagg ctgtggaagt taccggcacc acgcacttcc gcggtgttca ggcgcaagtc | 1020 |
| ggcgaagtgc tgaactggcg tgatgtcttt tggggtctgt cggacgctat ggcgaaaagt | 1080 |
| ccgaacagct gggtgggcgg tagcgttcag ccgaacctga attatggcct ggcctaccgc | 1140 |
| acctttatgg gcgtgggtta ccgcgtatt aaagaaatta ccagcaaac gctgggctct | 1200 |
| ggtctgatct acctgaactc atcggcagct gattggaaga tccggacgt tcgcccgtat | 1260 |
| ctggatcgtt acctgcgcgg cagtcgtggt attcaggcaa tcgatcgtgt caaactgctg | 1320 |
| aagctgctgt gggacgcggt gggcaccgaa tttgccggtc gtcatgaact gtatgaacgc | 1380 |
| aactacggcg gtgatcacga aggcattcgt gtgcagaccc tgcaagccta tcaggcaaat | 1440 |
| ggtcaagcgg cggcactgaa aggctttgcg aacagtgca tgagcgaata cgacctggat | 1500 |
| ggctggaccc gcccggacct gattaacccg ggcacctga | 1539 |

<210> SEQ ID NO 2
<211> LENGTH: 512
<212> TYPE: PRT
<213> ORGANISM: Saccharothrix espanaensis

<400> SEQUENCE: 2

Met Thr Ile Thr Ser Pro Ala Pro Ala Gly Arg Leu Asn Asn Val Arg
1               5                   10                  15

Pro Met Thr Gly Glu Glu Tyr Leu Glu Ser Leu Arg Asp Gly Arg Glu
            20                  25                  30

Val Tyr Ile Tyr Gly Glu Arg Val Asp Asp Val Thr Thr His Leu Ala
        35                  40                  45

```
Phe Arg Asn Ser Val Arg Ser Ile Ala Arg Leu Tyr Asp Val Leu His
 50                  55                  60

Asp Pro Ala Ser Glu Gly Val Leu Arg Val Pro Thr Asp Thr Gly Asn
 65                  70                  75                  80

Gly Gly Phe Thr His Pro Phe Phe Lys Thr Ala Arg Ser Ser Glu Asp
                     85                  90                  95

Leu Val Ala Ala Arg Glu Ala Ile Val Gly Trp Gln Arg Leu Val Tyr
                100                 105                 110

Gly Trp Met Gly Arg Thr Pro Asp Tyr Lys Ala Ala Phe Phe Gly Thr
            115                 120                 125

Leu Asp Ala Asn Ala Glu Phe Tyr Gly Pro Phe Glu Ala Asn Ala Arg
        130                 135                 140

Arg Trp Tyr Arg Asp Ala Gln Glu Arg Val Leu Tyr Phe Asn His Ala
145                 150                 155                 160

Ile Val His Pro Pro Val Asp Arg Asp Arg Pro Ala Asp Arg Thr Ala
                165                 170                 175

Asp Ile Cys Val His Val Glu Glu Thr Asp Ser Gly Leu Ile Val
                180                 185                 190

Ser Gly Ala Lys Val Val Ala Thr Gly Ser Ala Met Thr Asn Ala Asn
            195                 200                 205

Leu Ile Ala His Tyr Gly Leu Pro Val Arg Asp Lys Lys Phe Gly Leu
    210                 215                 220

Val Phe Thr Val Pro Met Asn Ser Pro Gly Leu Lys Leu Ile Cys Arg
225                 230                 235                 240

Thr Ser Tyr Glu Leu Met Val Ala Thr Gln Gly Ser Pro Phe Asp Tyr
                245                 250                 255

Pro Leu Ser Ser Arg Leu Asp Glu Asn Asp Ser Ile Met Ile Phe Asp
            260                 265                 270

Arg Val Leu Val Pro Trp Glu Asn Val Phe Met Tyr Asp Ala Gly Ala
        275                 280                 285

Ala Asn Ser Phe Ala Thr Gly Ser Gly Phe Leu Glu Arg Phe Thr Phe
    290                 295                 300

His Gly Cys Thr Arg Leu Ala Val Lys Leu Asp Phe Ile Ala Gly Cys
305                 310                 315                 320

Val Met Lys Ala Val Glu Val Thr Gly Thr Thr His Phe Arg Gly Val
                325                 330                 335

Gln Ala Gln Val Gly Glu Val Leu Asn Trp Arg Asp Val Phe Trp Gly
            340                 345                 350

Leu Ser Asp Ala Met Ala Lys Ser Pro Asn Ser Trp Val Gly Gly Ser
        355                 360                 365

Val Gln Pro Asn Leu Asn Tyr Gly Leu Ala Tyr Arg Thr Phe Met Gly
    370                 375                 380

Val Gly Tyr Pro Arg Ile Lys Glu Ile Ile Gln Gln Thr Leu Gly Ser
385                 390                 395                 400

Gly Leu Ile Tyr Leu Asn Ser Ser Ala Ala Asp Trp Lys Asn Pro Asp
                405                 410                 415

Val Arg Pro Tyr Leu Asp Arg Tyr Leu Arg Gly Ser Arg Gly Ile Gln
            420                 425                 430

Ala Ile Asp Arg Val Lys Leu Leu Lys Leu Leu Trp Asp Ala Val Gly
        435                 440                 445

Thr Glu Phe Ala Gly Arg His Glu Leu Tyr Glu Arg Asn Tyr Gly Gly
    450                 455                 460

Asp His Glu Gly Ile Arg Val Gln Thr Leu Gln Ala Tyr Gln Ala Asn
```

```
                465                 470                 475                 480
Gly Gln Ala Ala Ala Leu Lys Gly Phe Ala Glu Gln Cys Met Ser Glu
                    485                 490                 495

Tyr Asp Leu Asp Gly Trp Thr Arg Pro Asp Leu Ile Asn Pro Gly Thr
        500                 505                 510

<210> SEQ ID NO 3
<211> LENGTH: 510
<212> TYPE: DNA
<213> ORGANISM: Saccharothrix espanaensis

<400> SEQUENCE: 3
atgatgaccg tttatgatag cgcactgaca atggaagaaa ccaccctgcg tgatgcaatg      60
agccgttttg caaccggtgt tagcgttgtt accgttggtg gtgaacatac acatggtatg     120
accgcaaatg cctttacctg tgttagcctg gatccgcctc tggttctgtg ttgtgttgca     180
cgtaaagcaa ccatgcatgc agcaattgaa ggtgcacgtc gttttgcagt tagcgttatg     240
ggtggtgatc aagaacgtac cgcacgttat tttgcagata aacgtcgtcc gcgtggtcgt     300
gcacagtttg atgttgttga ttggcagcct ggtccgcata caggtgcacc gctgctgagc     360
ggtgcgctgg catggctgga atgtgaagtt gcacagtggc atgaaggtgg cgatcatacc     420
atttttctgg gtcgtgttct gggttgtcgt cgtggtccgg atagtccggc actgctgttt     480
tatggtagcg attttcatca gatccgctaa                                      510

<210> SEQ ID NO 4
<211> LENGTH: 169
<212> TYPE: PRT
<213> ORGANISM: Saccharothrix espanaensis

<400> SEQUENCE: 4

Met Met Thr Val Tyr Asp Ser Ala Leu Thr Met Glu Glu Thr Thr Leu
1               5                   10                  15

Arg Asp Ala Met Ser Arg Phe Ala Thr Gly Val Ser Val Val Thr Val
                20                  25                  30

Gly Gly Glu His Thr His Gly Met Thr Ala Asn Ala Phe Thr Cys Val
            35                  40                  45

Ser Leu Asp Pro Pro Leu Val Leu Cys Cys Val Ala Arg Lys Ala Thr
        50                  55                  60

Met His Ala Ala Ile Glu Gly Ala Arg Arg Phe Ala Val Ser Val Met
65                  70                  75                  80

Gly Gly Asp Gln Glu Arg Thr Ala Arg Tyr Phe Ala Asp Lys Arg Arg
                85                  90                  95

Pro Arg Gly Arg Ala Gln Phe Asp Val Val Asp Trp Gln Pro Gly Pro
            100                 105                 110

His Thr Gly Ala Pro Leu Leu Ser Gly Ala Leu Ala Trp Leu Glu Cys
        115                 120                 125

Glu Val Ala Gln Trp His Glu Gly Gly Asp His Thr Ile Phe Leu Gly
    130                 135                 140

Arg Val Leu Gly Cys Arg Arg Gly Pro Asp Ser Pro Ala Leu Leu Phe
145                 150                 155                 160

Tyr Gly Ser Asp Phe His Gln Ile Arg
                165

<210> SEQ ID NO 5
<211> LENGTH: 561
<212> TYPE: DNA
```

<213> ORGANISM: Pseudomonas fluorescens

<400> SEQUENCE: 5

```
atgaatgcag caaccgaaac caaagttcat gatctgctgg atgccgaagg tcgtgatgtt    60
cgtgatgcac gtgaactgcg taatgttctg ggtcagtttg caaccggtgt accgttatt    120
accacccgta ccgcagatgg tcgtaatgtt ggtgtgaccg caaatagctt tagcagcctg    180
agcctgagtc cggcactggt tctgtggtca ctggcacgta ccgcaccgag cctgaaagtt    240
ttttgtagcg caagccattt tgccattaat gtgctgggtg cacatcagct gcatctgagc    300
gaacagtttg cacgtgccgc agcagataaa tttgccggtg ttgcacatag ttatggtaaa    360
gcgggtgcac cggttctgga tgatgttgtt gcagttctgg tttgccgtaa tgttacccag    420
tatgaaggtg gtgatcatct gattttatc ggcgaaattg agcagtatcg ttatagcggt    480
gcagaaccgc tggtttttca tgcaggtcag tatcgtggtc tgggtagcaa tcgtgcagaa    540
agcgttctga aacatgaata a                                              561
```

<210> SEQ ID NO 6
<211> LENGTH: 186
<212> TYPE: PRT
<213> ORGANISM: Pseudomonas fluorescens

<400> SEQUENCE: 6

```
Met Asn Ala Ala Thr Glu Thr Lys Val His Asp Leu Leu Asp Ala Glu
1               5                   10                  15
Gly Arg Asp Val Arg Asp Ala Arg Glu Leu Arg Asn Val Leu Gly Gln
                20                  25                  30
Phe Ala Thr Gly Val Thr Val Ile Thr Thr Arg Thr Ala Asp Gly Arg
            35                  40                  45
Asn Val Gly Val Thr Ala Asn Ser Phe Ser Ser Leu Ser Leu Ser Pro
        50                  55                  60
Ala Leu Val Leu Trp Ser Leu Ala Arg Thr Ala Pro Ser Leu Lys Val
65                  70                  75                  80
Phe Cys Ser Ala Ser His Phe Ala Ile Asn Val Leu Gly Ala His Gln
                85                  90                  95
Leu His Leu Ser Glu Gln Phe Ala Arg Ala Ala Asp Lys Phe Ala
            100                 105                 110
Gly Val Ala His Ser Tyr Gly Lys Ala Gly Ala Pro Val Leu Asp Asp
        115                 120                 125
Val Val Ala Val Leu Val Cys Arg Asn Val Thr Gln Tyr Glu Gly Gly
    130                 135                 140
Asp His Leu Ile Phe Ile Gly Glu Ile Glu Gln Tyr Arg Tyr Ser Gly
145                 150                 155                 160
Ala Glu Pro Leu Val Phe His Ala Gly Gln Tyr Arg Gly Leu Gly Ser
                165                 170                 175
Asn Arg Ala Glu Ser Val Leu Lys His Glu
            180                 185
```

<210> SEQ ID NO 7
<211> LENGTH: 513
<212> TYPE: DNA
<213> ORGANISM: Escherichia coli

<400> SEQUENCE: 7

```
atgcaattag atgaacaacg cctgcgcttt cgtgacgcaa tggccagcct gtcggcagcg    60
gtaaatatta tcaccaccga gggcgacgcc ggacaatgcg ggattacggc aacggccgtc   120
```

```
tgctcggtca cggatacacc accatcgctg atggtgtgca ttaacgccaa cagtgcgatg      180
aacccggttt ttcagggcaa cggtaagttg tgcgtcaacg tcctcaacca tgagcaggaa      240
ctgatggcac gccacttcgc gggcatgaca ggcatggcga tggaagagcg ttttagcctc      300
tcatgctggc aaaaaggtcc gctggcgcag ccggtgctaa aaggttcgct ggccagtctt      360
gaaggtgaga tccgcgatgt gcaggcaatt ggcacacatc tggtgtatct ggtggagatt      420
aaaaacatca tcctcagtgc agaaggtcac ggacttatct actttaaacg ccgtttccat      480
ccggtgatgc tggaaatgga agctgcgatt taa                                   513

<210> SEQ ID NO 8
<211> LENGTH: 170
<212> TYPE: PRT
<213> ORGANISM: Escherichia coli

<400> SEQUENCE: 8

Met Gln Leu Asp Glu Gln Arg Leu Arg Phe Arg Asp Ala Met Ala Ser
1               5                   10                  15

Leu Ser Ala Ala Val Asn Ile Ile Thr Thr Glu Gly Asp Ala Gly Gln
            20                  25                  30

Cys Gly Ile Thr Ala Thr Ala Val Cys Ser Val Thr Asp Thr Pro Pro
        35                  40                  45

Ser Leu Met Val Cys Ile Asn Ala Asn Ser Ala Met Asn Pro Val Phe
    50                  55                  60

Gln Gly Asn Gly Lys Leu Cys Val Asn Val Leu Asn His Glu Gln Glu
65                  70                  75                  80

Leu Met Ala Arg His Phe Ala Gly Met Thr Gly Met Ala Met Glu Glu
                85                  90                  95

Arg Phe Ser Leu Ser Cys Trp Gln Lys Gly Pro Leu Ala Gln Pro Val
            100                 105                 110

Leu Lys Gly Ser Leu Ala Ser Leu Glu Gly Glu Ile Arg Asp Val Gln
        115                 120                 125

Ala Ile Gly Thr His Leu Val Tyr Leu Val Glu Ile Lys Asn Ile Ile
    130                 135                 140

Leu Ser Ala Glu Gly His Gly Leu Ile Tyr Phe Lys Arg Arg Phe His
145                 150                 155                 160

Pro Val Met Leu Glu Met Glu Ala Ala Ile
                165                 170
```